(12) United States Patent
May et al.

(10) Patent No.: US 11,241,709 B1
(45) Date of Patent: Feb. 8, 2022

(54) DISPENSER ACTUATOR ASSEMBLY

(71) Applicant: James Alexander Corporation, Blairstown, NJ (US)

(72) Inventors: Richard James May, Saylorsburg, PA (US); Jeffrey Rendano, Kunkletown, PA (US)

(73) Assignee: James Alexander Corporation, Blairstown, NJ (US)

( * ) Notice: Subject to any disclaimer, the term of this patent is extended or adjusted under 35 U.S.C. 154(b) by 131 days.

(21) Appl. No.: 16/598,660

(22) Filed: Oct. 10, 2019

Related U.S. Application Data

(60) Provisional application No. 62/744,457, filed on Oct. 11, 2018.

(51) Int. Cl.
*B05C 17/005* (2006.01)
*B05C 1/00* (2006.01)
*A61B 90/80* (2016.01)
*A61M 35/00* (2006.01)
*A61J 1/06* (2006.01)

(52) U.S. Cl.
CPC ........ *B05C 17/00586* (2013.01); *A61B 90/80* (2016.02); *A61J 1/065* (2013.01); *A61M 35/003* (2013.01); *B05C 1/00* (2013.01)

(58) Field of Classification Search
CPC ... B05C 1/00; B05C 17/00586; B05C 17/005; B05C 17/00583; A61B 90/80; A61M 35/003; A61M 35/006; A61J 1/065; A61J 1/06; B65D 35/00; B65D 35/08; B65D 35/22; A46B 11/0075; A46B 11/0041

USPC ............... 401/16–18, 23, 24, 34–36, 47
See application file for complete search history.

(56) References Cited

U.S. PATENT DOCUMENTS

| | | |
|---|---|---|
| 3,450,319 A | 6/1969 | Ray et al. |
| 5,538,353 A | 7/1996 | DeHavilland |
| D386,849 S | 11/1997 | DeHavilland |
| 5,772,346 A | 6/1998 | Edwards |
| 6,283,933 B1 * | 9/2001 | D'Alessio ........... A61M 35/003 401/132 |
| 6,315,165 B1 | 11/2001 | Regan |
| 6,536,975 B1 | 3/2003 | Tufts |
| 6,539,975 B2 | 4/2003 | Hedenberg |
| 6,641,319 B2 | 11/2003 | May |
| 6,729,786 B1 | 5/2004 | Tufts et al. |

(Continued)

*Primary Examiner* — David J Walczak
(74) *Attorney, Agent, or Firm* — Paul J. Nykaza; Schacht Law Office, Inc.

(57) ABSTRACT

A dispenser actuator assembly (100) has base member (102) and an actuator arm (104) that is configured to crush a glass ampoule assembly (10). The glass ampoule assembly (10) has a rupturable glass ampoule (12) containing a flowable material (M). The glass ampoule (12) is contained within an outer container (14), the outer container (14) having a first open end (22) and a second closed end (24). The glass ampoule assembly (10) has an applicator (16) positioned in the first open end (22). The dispenser actuator assembly (100) has the base member (102) that is configured to mount on the outer container (14). The actuator arm (104) is pivotally connected to the base member (102). The actuator arm (104) is pivotable from a first position to a second position that is configured to engage the outer container (14) to crush the glass ampoule (12) wherein the flowable material (M) is dispensed from the glass ampoule assembly (10).

27 Claims, 14 Drawing Sheets

(56) References Cited

U.S. PATENT DOCUMENTS

| | | |
|---|---|---|
| 6,991,393 B2 | 1/2006 | Tufts et al. |
| 6,991,394 B2 | 1/2006 | Tufts et al. |
| 7,182,536 B2 | 2/2007 | Tufts et al. |
| 7,241,065 B2 | 7/2007 | Tufts et al. |
| 7,306,390 B2 | 12/2007 | Quintero et al. |
| 7,422,388 B2 | 9/2008 | Tufts et al. |
| 7,516,872 B2 | 4/2009 | Boone et al. |
| 7,581,899 B2 | 9/2009 | May et al. |
| 7,824,122 B2 | 11/2010 | Flores et al. |
| 7,909,808 B2 | 3/2011 | Stenton |
| 7,976,234 B2 | 7/2011 | May |
| 7,993,066 B2 | 8/2011 | Flores et al. |
| D651,339 S | 12/2011 | Kirk, III et al. |
| 8,323,260 B2 | 12/2012 | Stenton |
| 8,342,765 B2 | 1/2013 | Stenton |
| 8,403,178 B2 | 3/2013 | May et al. |
| 8,491,212 B2 * | 7/2013 | Castel ............ A45D 34/04 401/133 |
| 8,518,076 B2 | 8/2013 | Stenton |
| 8,702,751 B2 | 4/2014 | Stenton |
| 8,794,858 B2 | 8/2014 | Kirk, III et al. |
| 8,801,312 B2 | 8/2014 | Guzman et al. |
| 8,807,859 B2 | 8/2014 | Stenton |
| 8,864,399 B2 | 10/2014 | Guzman et al. |
| 9,089,870 B2 | 7/2015 | Frazier |
| 9,119,946 B2 | 9/2015 | Dokken et al. |
| 9,265,923 B2 | 2/2016 | Boone et al. |
| 9,486,829 B2 | 11/2016 | Kirk, III et al. |
| 9,675,787 B2 | 6/2017 | Guzman |
| 10,392,163 B2 | 8/2019 | May et al. |
| 10,518,930 B2 | 12/2019 | May et al. |
| 10,526,110 B2 | 1/2020 | May et al. |
| 10,543,956 B2 | 1/2020 | May et al. |
| 10,603,019 B2 | 3/2020 | Miller et al. |
| 10,669,065 B2 | 6/2020 | May et al. |
| 10,689,152 B2 | 6/2020 | May et al. |
| 2003/0068189 A1 * | 4/2003 | Tsaur ............ B65D 81/3283 401/133 |
| 2004/0254561 A1 | 12/2004 | Stenton |
| 2005/0111900 A1 | 5/2005 | Fazzolari et al. |
| 2008/0046004 A1 | 2/2008 | Stenton |
| 2008/0167681 A1 | 7/2008 | Stenton |
| 2008/0195040 A1 | 8/2008 | Clark et al. |
| 2009/0311030 A1 | 12/2009 | Stenton |
| 2013/0004230 A1 | 1/2013 | Kirk, III et al. |
| 2014/0133895 A1 * | 5/2014 | Dockery ............ A45D 40/24 401/6 |
| 2015/0306362 A1 | 10/2015 | Battaglia |
| 2017/0049210 A1 | 2/2017 | Kirk, III et al. |
| 2017/0354406 A1 | 12/2017 | Miller et al. |
| 2018/0050858 A1 | 2/2018 | May et al. |
| 2018/0065776 A1 | 3/2018 | May et al. |
| 2018/0065783 A1 | 3/2018 | May et al. |

\* cited by examiner

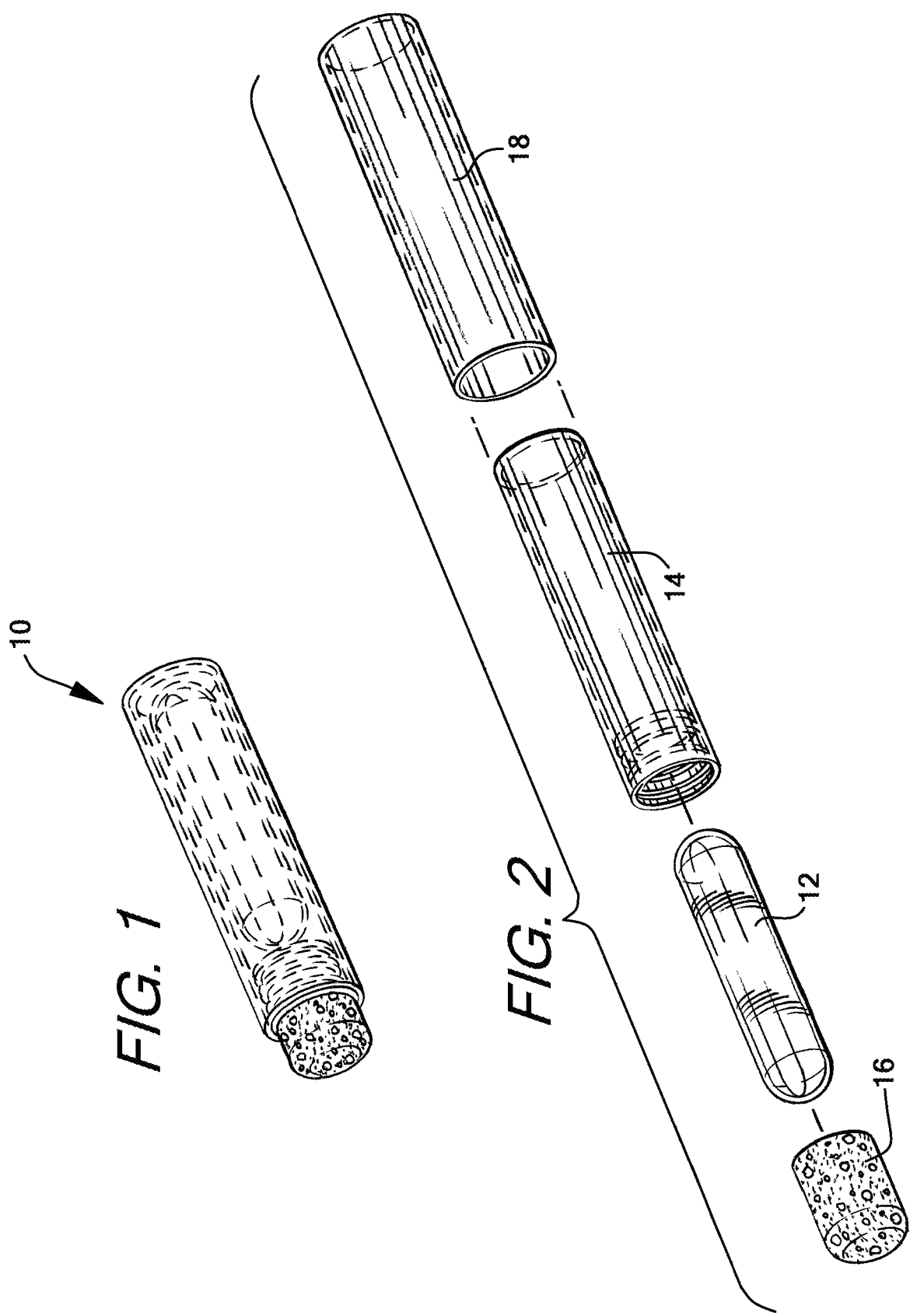

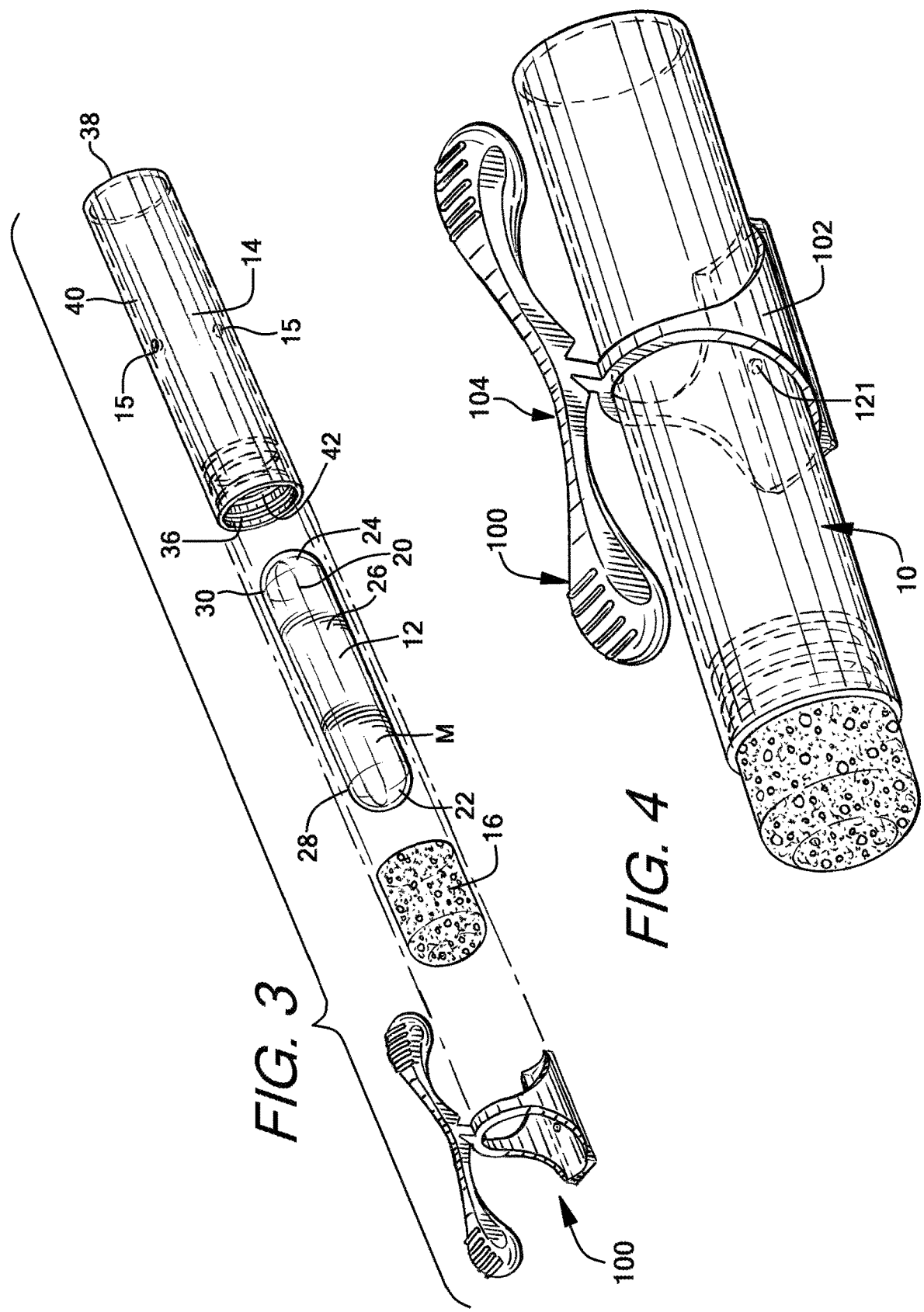

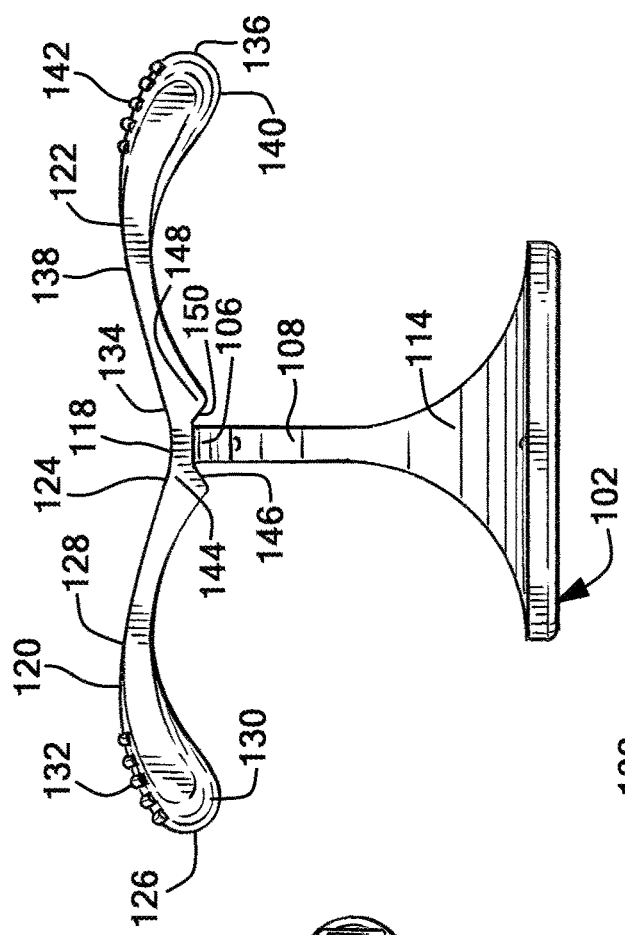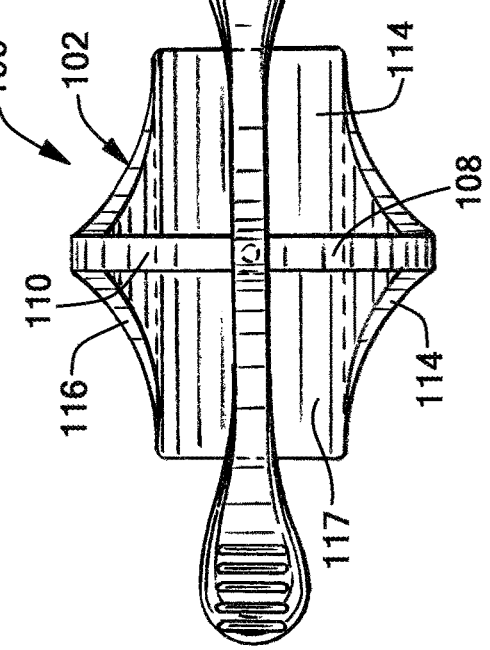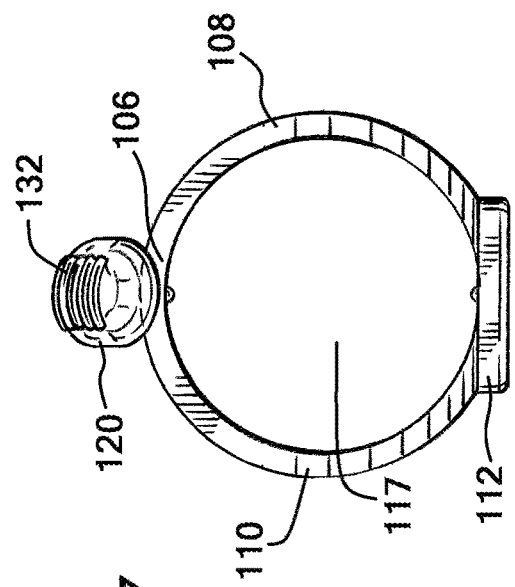

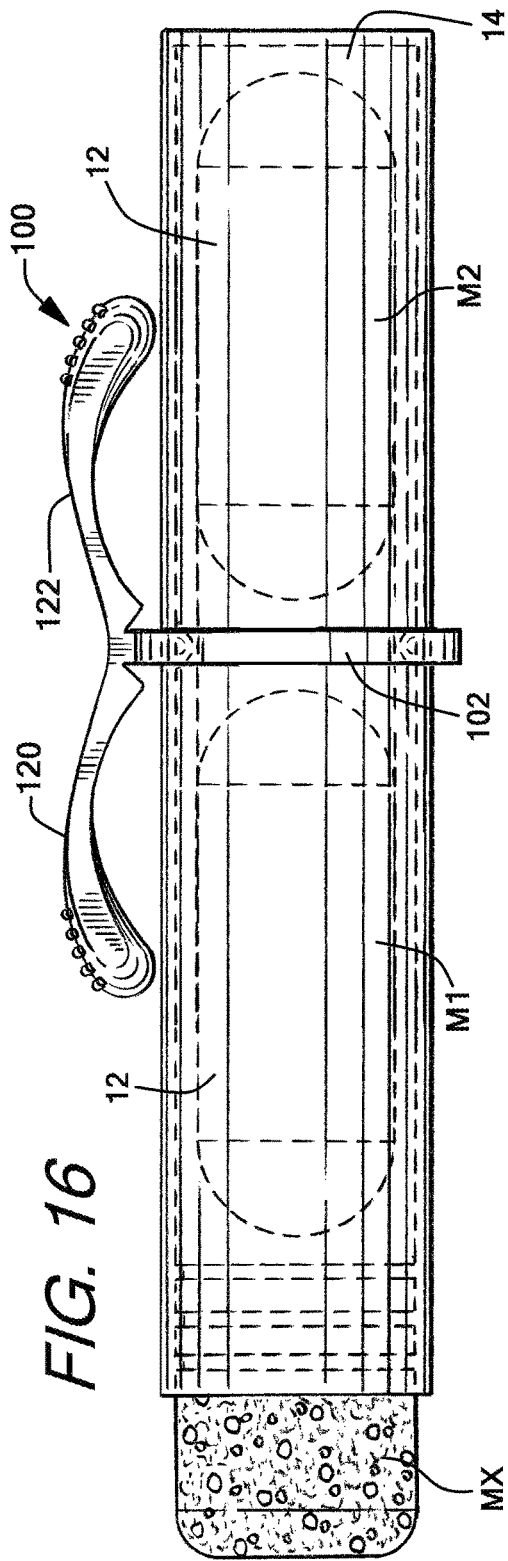
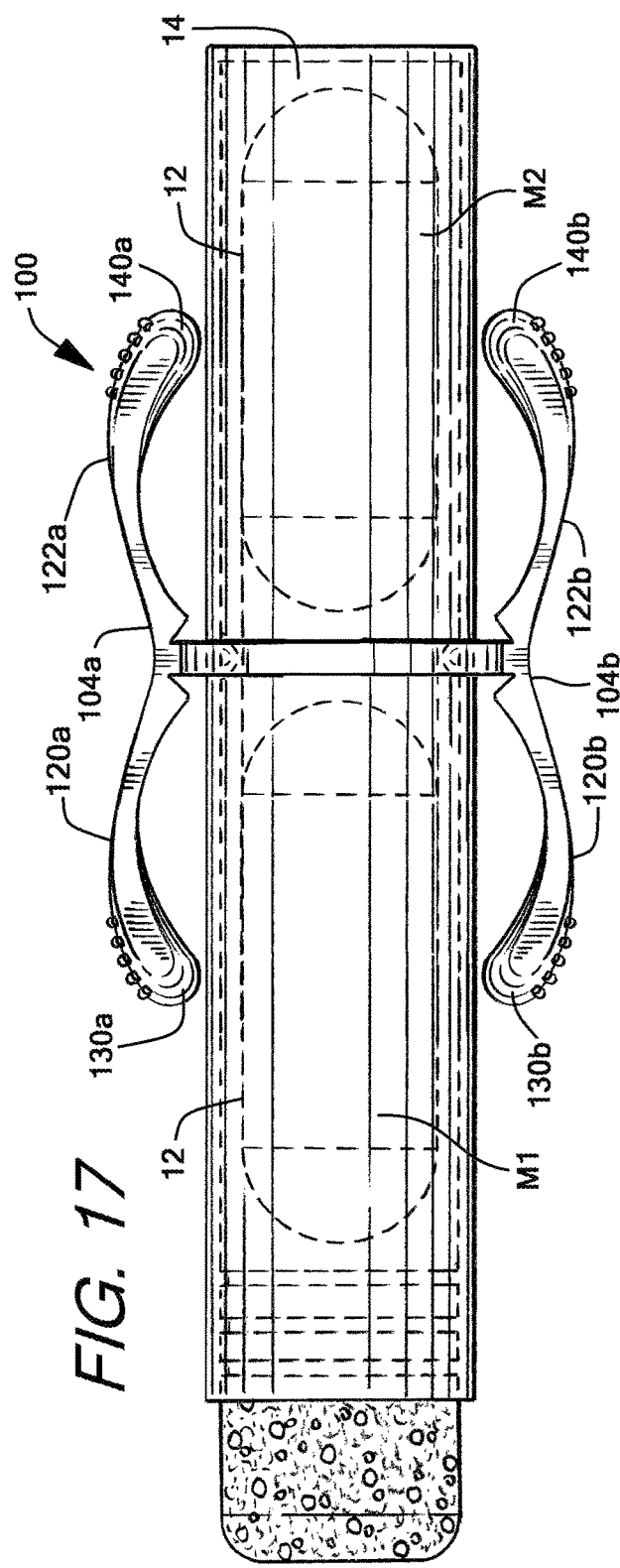

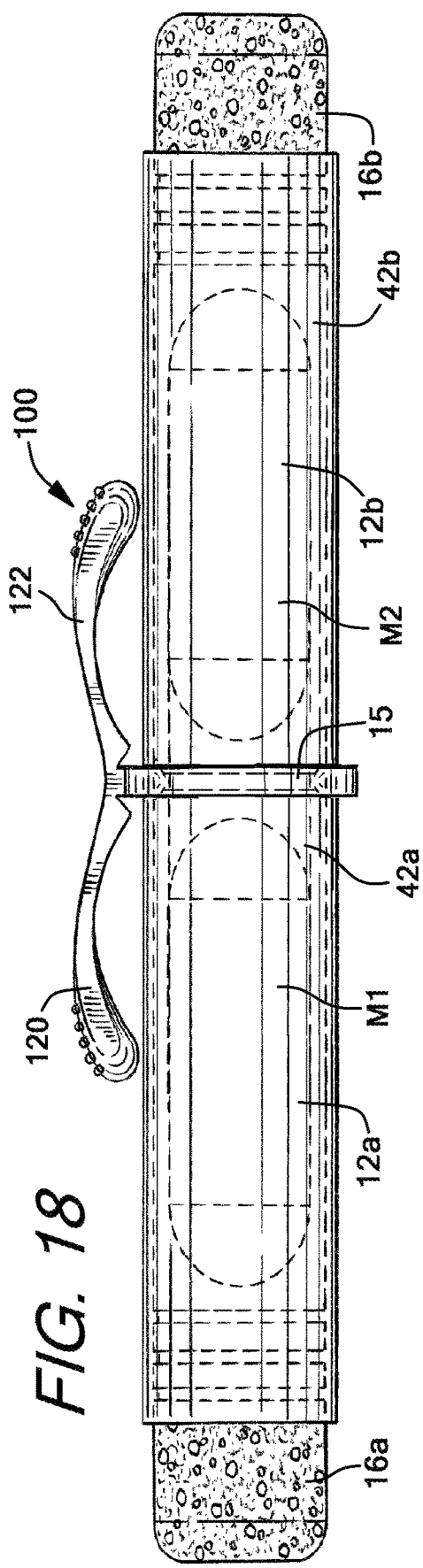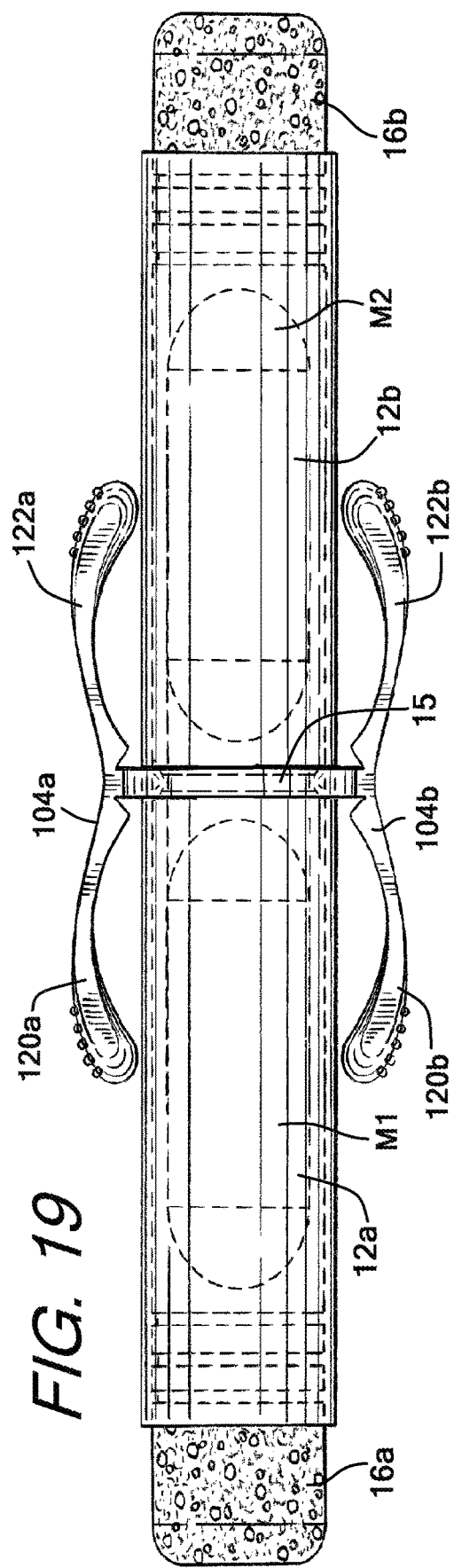

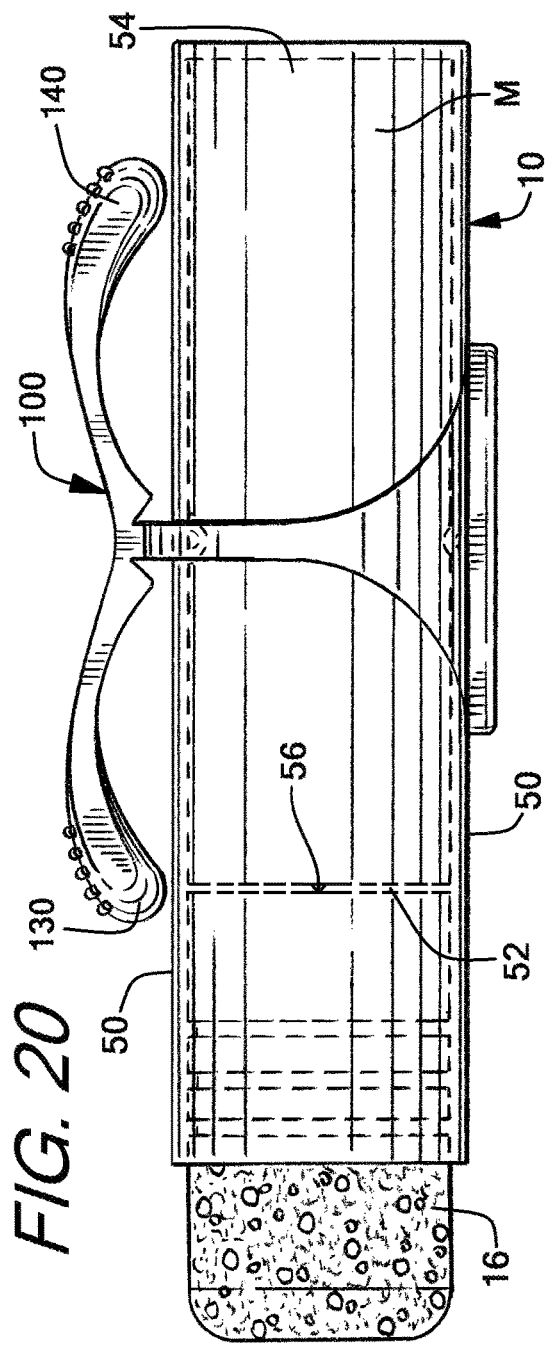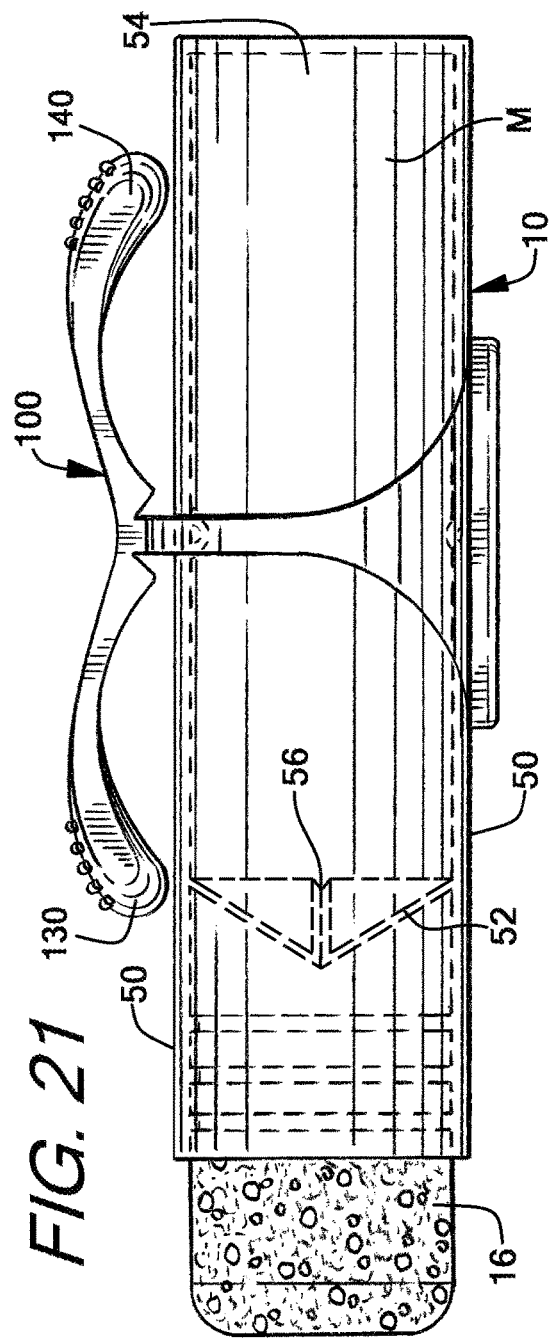

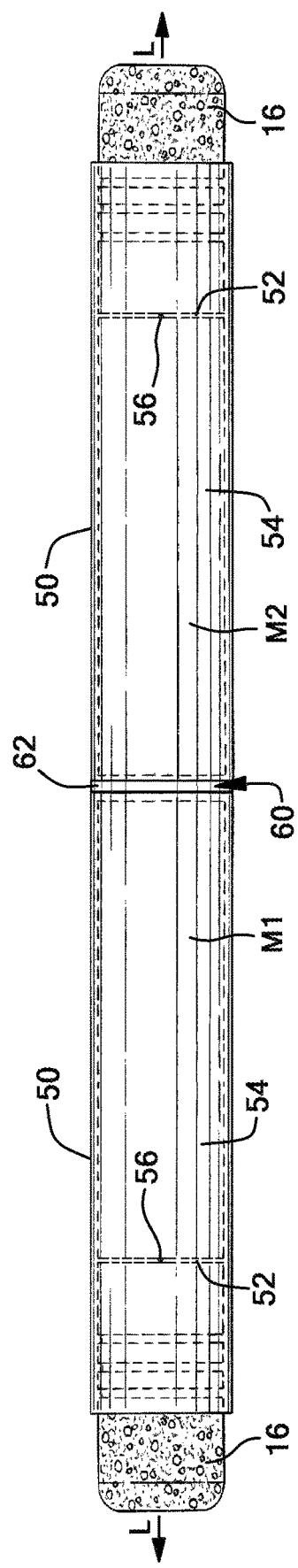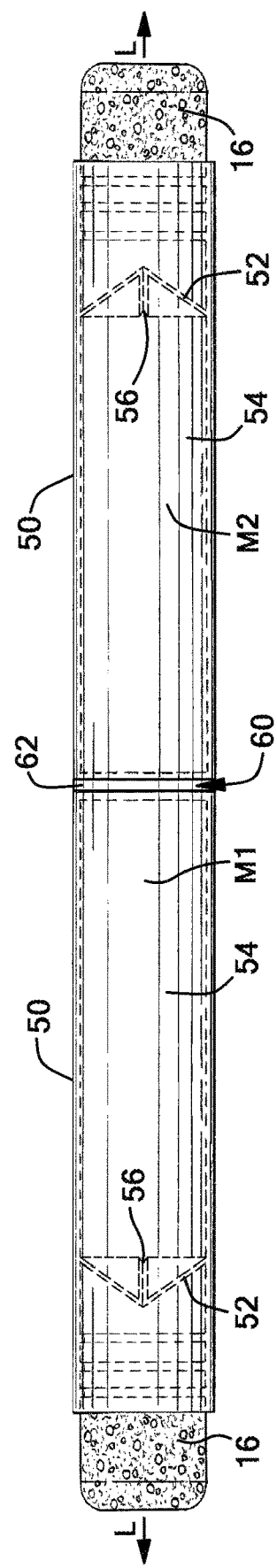

DISPENSER ACTUATOR ASSEMBLY

CROSS-REFERENCE TO RELATED APPLICATIONS

The present application claims the benefit of U.S. Patent Application No. 62/744,457, filed on Oct. 11, 2018, which application is incorporated in its entirety by reference herein and made a part hereof.

FEDERALLY SPONSORED RESEARCH OR DEVELOPMENT

None.

TECHNICAL FIELD

The invention relates generally to an actuator assembly for a dispenser and more particularly, to an dispenser actuator assembly having a base configured to mount on a crushable glass ampoule assembly wherein an actuator arm is operably connected to the base and dimensioned to crush the glass ampoule assembly.

BACKGROUND OF THE INVENTION

Dispensers such as glass ampoule assemblies are well known in the art and are often designed to be single-use disposable dispensers. A glass ampoule assembly typically includes a rupturable container such as a glass ampoule that contains a flowable material to be dispensed. The glass ampoule is contained in an outer container that may be made from a plastic material and having a closed end and an open end. The glass ampoule assembly may further include an applicator such as a swab that fits in the open end of the outer container. The applicator assists in dispensing the flowable material after the glass ampoule is crushed. The glass ampoule assembly may also include a cover member such as a cardboard sleeve that is used when initially storing and transporting the glass ampoule assembly wherein the applicator end of the glass ampoule assembly is inserted into the cardboard sleeve. An opposite end of the glass ampoule assembly may be inserted into the cardboard sleeve wherein the applicator extends out of the sleeve. A user may squeeze the cardboard sleeve via finger pressure to deflect the plastic outer container and crush the glass ampoule wherein the flowable material is dispensed from the applicator.

Attempts have been made to design ampoule holders that assist in rupturing the ampoule. These designs, however, have been high in cost and cumbersome in design and operation. Furthermore, the glass ampoule is not crushed in an optimum location wherein dispensing of the flowable material becomes problematic because of obstruction from fractured pieces of the glass ampoule.

Additional problems have also been experienced with the glass ampoule assemblies. In some instances, users do not have sufficient finger strength to crush the glass ampoule. For example, users of advanced age oftentimes have arthritis and cannot crush the glass ampoule. In other instances, upon rupturing the glass ampoule, glass shards puncture through the outer container and injure the user. In still other instances, the glass ampoule is typically crushed at a central location of the glass ampoule. Rupturing the ampoule at the central location leaves a dome-shaped end portion of the glass ampoule intact. The dome-shaped end portion may end up positioned at the applicator wherein the flow of the flowable material is restricted from the dispenser.

While glass ampoule assemblies and associated ampoule holders/actuators according to the prior art provide a number of advantageous features, they nevertheless have certain limitations. The present invention seeks to overcome certain of these limitations and other drawbacks of the prior art, and to provide new features and new uses not heretofore available. A full discussion of the features and advantages of the present invention is deferred to the following detailed description, which proceeds with reference to the accompanying drawings.

SUMMARY OF THE INVENTION

The present invention provides a dispenser actuator assembly designed to actuate a dispenser to dispense a flowable material from the dispenser.

According to a first aspect of the invention, a dispenser actuator assembly is provided for actuating a dispenser such as a glass ampoule assembly. The glass ampoule assembly has a rupturable glass ampoule containing a flowable material. The glass ampoule is contained within an outer container. The outer container has a first open end and a second closed end. The glass ampoule assembly has an applicator positioned in the first open end. The dispenser actuator assembly has a base member configured to mount on the outer container. An actuator arm is pivotally connected to the base member. The actuator arm is pivotable from a first position to a second position that is configured to engage the outer container to crush the glass ampoule wherein the flowable material is dispensed from the glass ampoule assembly According to another aspect of the invention, a dispenser actuator assembly for actuating a dispenser is provided, The dispenser may be in the form of a glass ampoule assembly having a rupturable glass ampoule containing a flowable material. The glass ampoule has an interface area defined generally between a dome-shaped closed end and a generally cylindrical central portion. The glass ampoule is contained within an outer container, the outer container having a first open end and a second closed end. The glass ampoule assembly has an applicator positioned in the first open end. The dispenser actuator assembly has a base member configured to receive the outer container and mount on the outer container. An actuator arm has a first arm implement and a central hub, the central hub connected to the base member. The first arm implement has a first intermediate segment having a curvilinear configuration extending away from the base member. The first arm implement has a first depending protrusion at a first distal end, the first depending protrusion configured to be positioned proximate the interface area of the glass ampoule. The first arm implement is pivotable with respect to the base member from a first neutral position to a first actuating position that is configured to engage and deflect the outer container inwardly to crush the glass ampoule at the interface area wherein the flowable material is released from the glass ampoule.

According to a further aspect of the invention, the base member is dimensioned to fit circumjacently around the glass ampoule assembly in an interference fit. The base member may be an annular ring. The base member defines a platform segment dimensioned for a user's finger to engage against the platform segment when the user crushes the glass ampoule. The base member has a first flared wall portion and a second flared wall portion positioned in opposed relation and connected to the platform segment.

According another aspect of the invention, the base member has a locating structure that is configured to cooperate with the glass ampoule assembly when the actuator assembly is mounted on the glass ampoule assembly.

According to a further aspect of the invention, the base member defines an opening therethrough.

According to yet another aspect of the invention, the first depending protrusion of the first arm implement is configured to be spaced from the outer container when the base member is connected to the glass ampoule assembly.

According to another aspect of the invention, a proximal end of the first arm implement is connected to the central hub, wherein a first hinge is defined proximate the proximal end of the first arm implement and the central hub, the first hinge defining a cut-out portion that extends into the first arm implement.

According to another aspect of the invention, the actuator arm has a second arm implement. The central hub is positioned between the first arm implement and the second arm implement. The second arm implement has a second intermediate segment having a curvilinear configuration extending away from the base member generally opposite the first arm implement, the second arm implement having a second depending protrusion at a second distal end.

According to a further aspect of the invention, the second depending protrusion of the second arm implement is configured to be spaced from the outer container when the base member is connected to the glass ampoule assembly.

According to another aspect of the invention, a proximal end of the second arm implement is connected to the central hub, wherein a second hinge is defined proximate the proximal end of the second arm implement and the central hub, the second hinge defining a cut-out portion that extends into the second arm implement.

According to another aspect of the invention, the second arm implement is pivotable with respect to the base member from a second neutral position to a second actuating position that is configured to engage and deflect the outer container inwardly to assist in manipulating the flowable material into the applicator to be dispensed from the glass ampoule assembly.

According to yet another aspect of the invention, the first arm implement is pivotable independently of the second arm implement.

According to another aspect of the invention, the actuator assembly has a second actuator arm having a first arm implement and a second central hub. The second central hub is connected to the base member generally opposite to the central hub. The first arm implement of the second actuator arm has a first intermediate segment having a curvilinear configuration extending away from the base member, the first arm implement of the second actuator arm having a first depending protrusion at a first distal end, the first depending protrusion configured to be positioned proximate the interface area of the glass ampoule. The first arm implement of the second actuator arm is pivotable with respect to the base member from a first neutral position to a first actuating position that is configured to engage and deflect the outer container inwardly to crush the glass ampoule at the interface area wherein the flowable material is released from the glass ampoule.

According to a further aspect of the invention, the second actuator arm has a second arm implement. The second central hub is positioned between the first arm implement and the second arm implement of the second actuator arm. The second arm implement of the second actuator arm has a second intermediate segment having a curvilinear configuration extending away from the base member generally opposite the first arm implement. The second arm implement of the second actuator arm has a second depending protrusion at a second distal end. The second arm implement of the second actuator arm is pivotable with respect to the base member from a second neutral position to a second actuating position that is configured to engage and deflect the outer container inwardly to assist in manipulating the flowable material into the applicator to be dispensed from the glass ampoule assembly.

According to a further aspect of the invention, the first arm implement of the first actuator arm is positioned generally opposite to the first arm implement of the second actuator arm. The second arm implement of the first actuator arm is positioned generally opposite to the second arm implement of the second actuator arm. The first depending protrusion of the first arm implement of the first actuator arm and the first depending protrusion of the first arm implement of the second actuator arm are configured to engage and deflect the outer container inwardly to crush the glass ampoule at the interface area. The second depending protrusion of the second arm implement of the first actuator arm and the second depending protrusion of the second arm implement of the second actuator arm are configured to engage and deflect the outer container inwardly to assist in manipulating the flowable material into the applicator to be dispensed from the glass ampoule assembly.

According to another aspect of the invention, a dispenser and actuator assembly is provided. The dispenser is in the form of a plastic ampoule assembly. The plastic ampoule assembly has a container having a first chamber and a second chamber, the first chamber containing a flowable material, the second chamber defining an open end. A membrane is disposed within the container separating the first chamber and the second chamber, the membrane having a thickness and a weld seam, the weld seam having a thickness less than the thickness of the membrane. An applicator is positioned in the open end. The actuator assembly has a base member having an annular ring, the annular ring mounted on the container. An actuator arm has a first arm implement and a central hub, the central hub connected to the base member. The first arm implement has a first intermediate segment having a curvilinear configuration extending away from the base member. The first arm implement has a first depending protrusion at a first distal end, the first depending protrusion configured to be positioned proximate the membrane of the plastic ampoule assembly. The first arm implement is pivotable with respect to the base member from a first neutral position to a first actuating position that is configured to engage and deflect the container inwardly to fracture the weld seam of the membrane wherein the flowable material is released from the plastic ampoule assembly.

According to another aspect of the invention, a dispenser is provided in the form of a first plastic ampoule assembly and a second plastic ampoule assembly. The first plastic ampoule assembly has a container having a first chamber and a second chamber, the first chamber containing a first flowable material. The first chamber has a closed end, and the second chamber defines an open end. A membrane is disposed within the container separating the first chamber and the second chamber. The membrane has a thickness and a weld seam, the weld seam having a thickness less than the thickness of the membrane. An applicator is positioned in the open end. The second plastic ampoule assembly has a container having a first chamber and a second chamber, the first chamber containing a second flowable material. The first chamber has a closed end, and the second chamber defines an open end. A membrane is disposed within the container separating the first chamber and the second chamber, the membrane having a thickness and a weld seam, the weld seam having a thickness less than the thickness of the membrane. An applicator is positioned in the open end. The closed end of the first chamber of the first plastic ampoule is connected to the closed end of the first chamber of the second plastic ampoule and defining a connection area.

According to a further aspect of the invention, the first plastic ampoule and the second plastic ampoule extend away from each other linearly along a longitudinal axis.

According to yet another aspect of the invention, the closed end of the first chamber of the first plastic ampoule has a generally first circular configuration and the closed end of the first chamber of the second plastic ampoule has a generally second circular configuration, wherein the first circular configuration is dimensioned to coincide with a dimension of the second circular configuration.

According to a further aspect of the invention, the connection between the first plastic ampoule and the second plastic ampoule is an adhesive connection. Alternatively, the connection between the first plastic ampoule and the second plastic ampoule is a spin-welded connection.

According to another aspect of the invention, a dispenser and actuator assembly are provided. The dispenser is in the form of a glass ampoule assembly. The glass ampoule assembly has a first crushable glass ampoule containing a first flowable material and a second crushable glass ampoule containing a second flowable material. A resilient plastic outer container has a first open end and a second open end, and the outer container receives the first glass ampoule and the second glass ampoule. A first applicator is positioned in the first open end, and a second applicator is positioned in the second open end. An actuator assembly has a base member having an annular ring, the annular ring receiving the outer container and mounted on the outer container. An actuator arm has a first arm implement and a central hub, the central hub connected to the base member. The first arm implement has a first intermediate segment having a curvilinear configuration extending away from the base member, the first arm implement having a first depending protrusion at a first distal end. The first depending protrusion is positioned proximate the first glass ampoule. The actuator arm has a second arm implement, the central hub positioned between the first arm implement and the second arm implement. The second arm implement has a second intermediate segment having a curvilinear configuration extending away from the base member generally opposite the first arm implement. The second arm implement has a second depending protrusion at a second distal end, the second depending protrusion positioned proximate the second glass ampoule. The first arm implement is pivotable with respect to the base member from a first neutral position to a first actuating position to engage and deflect the outer container inwardly to crush the first glass ampoule wherein the first flowable material is released from the first glass ampoule and into the first applicator to be dispensed. The second arm implement is pivotable with respect to the base member from a second neutral position to a second actuating position to engage and deflect the outer container inwardly to crush the second glass ampoule wherein the second flowable material is released from the second glass ampoule and into the second applicator to be dispensed.

According to a further aspect of the invention, the outer container has a dividing wall defining a first chamber having the first open end and defining a second chamber having the second open end, the first glass ampoule positioned in the first chamber and the second glass ampoule positioned in the second chamber.

According to a further aspect of the invention, the actuator assembly is slidably moveable along the outer container.

According to another aspect of the invention, a glass ampoule assembly is provided. The glass ampoule assembly has a crushable glass ampoule containing a flowable material. A resilient plastic outer container has a first open end and a second open end. The outer container receives the glass ampoule through one of the first open end and the second open end. A first applicator is positioned in the first open end, the first applicator having a first applicator structure. A second applicator is positioned in the second open end, the second applicator having a second applicator structure. The second applicator structure is different from the first applicator structure. The first applicator is a first swab assembly having a generally constant diameter along a length of the first swab assembly. The second applicator is a second swab assembly that is tapered along a length of the second swab assembly. The second swab assembly has an apex at a distal end. In another embodiment, the first applicator is a swab assembly and the second applicator is a dropper assembly.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 1 is a perspective view of a dispenser in the form of a glass ampoule assembly;

FIG. 2 is an exploded view of the glass ampoule assembly of FIG. 1 FIG. 3 is an exploded view of the glass ampoule assembly but without a cover member and also showing an dispenser actuator assembly according to an exemplary embodiment of the present invention;

FIG. 4 is a perspective view of the dispenser actuator assembly shown in FIG. 3 and mounted on a glass ampoule assembly;

FIG. 5 is a top plan view of the dispenser actuator assembly shown in FIG. 3;

FIG. 6 is a side elevation view of the dispenser actuator assembly shown in FIG. 3;

FIG. 7 is an end view of the dispenser actuator assembly shown in FIG. 3;

FIG. 16 is a side elevation view of an alternative embodiment of the dispenser actuator assembly mounted on a tandem glass ampoule assembly;

FIG. 17 is a side elevation view of an alternative embodiment of the dispenser actuator assembly mounted on a tandem glass ampoule assembly;

FIG. 18 is a side elevation view of an alternative embodiment of the dispenser actuator assembly mounted on a tandem glass ampoule assembly with multiple applicators;

FIG. 19 is a side elevation view of an alternative embodiment of the dispenser actuator assembly mounted on a tandem glass ampoule assembly with multiple applicators;

FIG. 20 is a side elevation view of the dispenser actuator assembly used with an alternative dispenser in the form of a plastic ampoule assembly having a planar membrane;

FIG. 21 is a side elevation view of the dispenser actuator assembly used with an alternative dispenser in the form of a plastic ampoule assembly having a conical membrane;

FIG. 24 is a side elevation view of an alternative embodiment of a dispenser according to an exemplary embodiment of the invention; and FIG. 25 is a side elevation view of a further alternative embodiment of a dispenser according to an exemplary embodiment of the invention.

DETAILED DESCRIPTION OF THE PREFERRED EMBODIMENT

Figure 8:
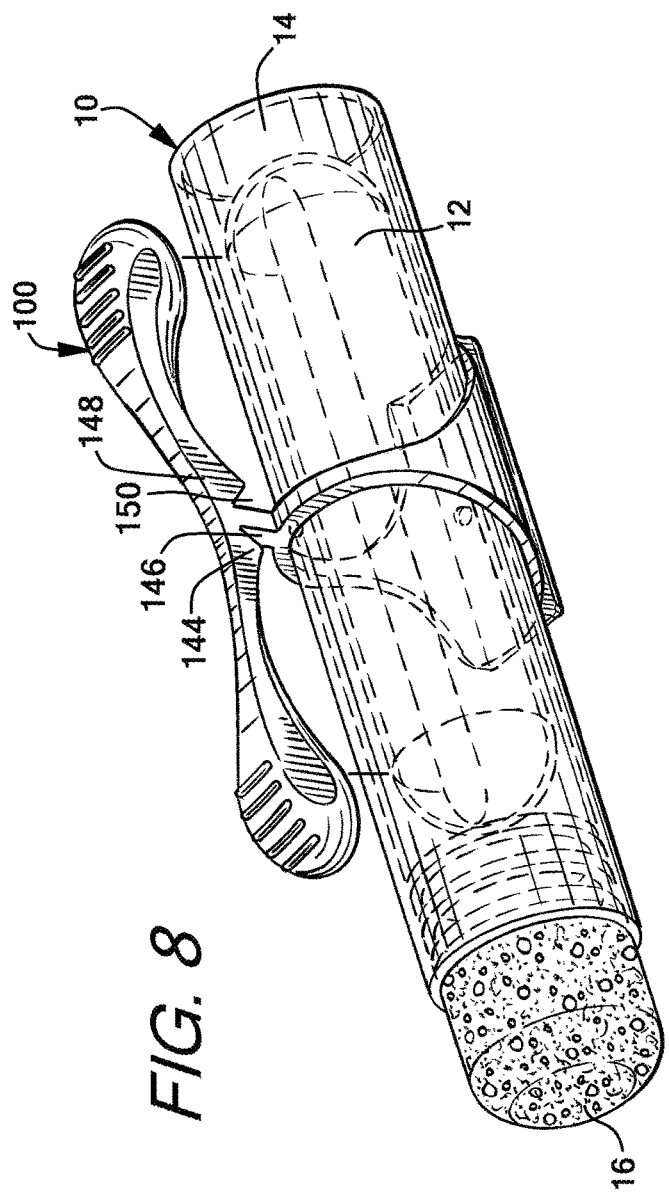
FIG. 8 is a perspective view of the dispenser actuator assembly mounted on a glass ampoule assembly.

While this invention is susceptible of embodiments in many different forms, there are shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present invention discloses a dispenser actuator assembly that can be used in conjunction with a dispenser to activate the dispenser and dispense flowable material from the dispenser. The dispenser actuator assembly may also be referred to as an ampoule actuator assembly. The dispenser can take various forms and in one particular application, the dispenser may take the form of a glass ampoule assembly. The dispenser in the form of the glass ampoule assembly will be described followed by describing the dispenser actuator assembly including the connection of the components and actuating the dispenser.

FIG. 1 discloses a dispenser used in accordance with an exemplary embodiment of the invention and generally designated with the reference numeral 10. As further shown in FIG. 2, the dispenser 10 generally includes a first container 12, a second container 14 and an applicator assembly 16. A cover member 18 (FIG. 2) may optionally be utilized as explained in greater detail below. In this configuration, the dispenser 10 may also be referred to as a glass ampoule assembly 10. It is understood that the dispenser 10 or glass ampoule assembly 10 may take different forms as well such as other devices having rupturable containers.

FIGS. 1-3 show the first container 12. The first container 12 is generally structured to contain the flowable material M to be dispensed from the dispenser 10. The flowable material M is typically a liquid in an exemplary embodiment. It is understood, however, that flowable materials in other forms could be used such as powders. The first container 12 defines a chamber 20 therein that contains the flowable material M. The first container 12 has a first end 22 that is closed and also has a second end 24 that is closed as well as an intermediate section 26 therebetween. The intermediate section 26 of the first container 12 is generally cylindrical in shape and has a generally circular cross-section. The first end 22 is generally dome-shaped and the second end 24 is generally dome-shaped. Other configurations are also possible. As further shown in FIGS. 1-3, a first interface area 28 is defined at or proximate the juncture between the first dome-shaped end 22 and an end of the intermediate section 26. Similarly, a second interface area 30 is defined at or proximate the juncture between the second dome-shaped end 24 and the other end of the intermediate section 26. Thus, the first interface area 28 is at the location of the first container 12 transitions from an end of the intermediate section 26 to the dome shape of the first end 22. Similarly, the second interface area 30 is at the location of the first container 12 transitions from an end of the intermediate section 26 to the dome shape of the second end 24. The first container 12 may be dimensioned to have a diameter and length to define the first chamber 20 in a size to contain a desired amount of the flowable material M. The first container 12 is designed to be crushable, fracturable or rupturable as described in greater detail below. In an exemplary embodiment, the first container 12 is made from a rigid fracturable material such as glass. The first container 12 may be a traditional glass ampoule. Glass ampoules are known in the art and provide a hermetically-sealed chamber for containing the flowable material M. In one exemplary embodiment, a single glass ampoule 12 is used. It is understood that the dispenser 10 could be configured to use multiple glass ampoules 12 as described in greater detail below.

FIGS. 1-3 further show the second container 14, or outer container 14. The second container 14 has an open first end 36 and a closed second end 38, and an outer wall 40 therebetween. The outer wall 40 of the second container 14 defines a second chamber 42. The second chamber 42 is cooperatively dimensioned and configured to receive at least a portion of the first container 12, and typically the entire first container 12 is received in the second container 14. Thus, in an exemplary embodiment, the second container 14 is generally cylindrical and receives the first container 12 in a generally snug-fit configuration. The second container 14 is made from a flexible resilient material such as plastic in an exemplary embodiment. The second container 14 may be transparent or translucent plastic wherein the flowable material M in the first container 12 can be visible through the second container 14 and also through the first container 12. The second container 14 may also be made from opaque material when the flowable material M or other contents are light sensitive.

FIGS. 1-3 further show the applicator 16 or applicator assembly 16. The applicator assembly 16 assists in dispensing the flowable material M from the dispenser 10 to a receiving surface. Any applicator assembly 16 that performs this function can be used in the dispenser 10. Thus, the applicator assembly 16 can take various forms including a swab assembly, a dropper assembly, a roller ball or a brush assembly. The swab applicator may also take various forms such as being made from absorbent, porous material, and that relies on a wicking action to dispense the flowable material M. It is also understood that the applicator assembly 16 may have a filter member operably associated therewith. The filter member is structured to allow passage of the flowable material M through the filter member while preventing passage of glass shards from the fractionated glass ampoule 12. The filter member may be positioned between the first end 22 of the first container 12 and the applicator assembly 16.

In one exemplary embodiment, the applicator assembly 16 is in the form of a swab assembly. The applicator 16 can be formed from a variety of materials capable of distributing the flowable material M from the applicator 16 to a receiving surface. In addition to a swab assembly, the applicator assembly 16 can take other forms such as a dropper assembly or roller assembly etc.

In another exemplary embodiment, the applicator assembly 16 can be in the form of a dropper assembly. The applicator assembly 16 has a base having a protrusion extending therefrom at one end. The base has a dropper tip member extending from an opposite end. The applicator assembly 16 has a central conduit extending therethrough from a distal end of the protrusion to a distal end of the dropper tip member. The protrusion has a generally annular configuration and is dimensioned to be received by the open first end 36 of the second container 14. In an exemplary embodiment, the protrusion and the open first end 36 of the second container 14 are cooperatively dimensioned wherein the protrusion 34 is received in the open first end 36 in an interference fit. As further described below, the applicator assembly 16 is configured to receive the flowable material M from the fractionated first container 12 and to dispense the flowable material M onto a receiving surface.

If desired, the dispenser 10 may also utilize the cover member 18. The cover member 18 is designed to initially cover the applicator assembly 16 prior to activating the dispenser 10 as can be appreciated from FIG. 2. The cover member 18 is dimensioned to fit snugly over the applicator assembly 16 and extend over a portion of the dispenser 10. One end of the cover member 18 may be closed although it is understood that both ends of the cover member 18 could be open ends. When preparing to activate the dispenser 10, the cover member 18 is removed from the dispenser 10. In prior art applications, an end of the dispenser 10 opposite of the applicator assembly 16 is inserted into the cover member 18. With the present invention as described in further detail below, the cover member 18 is not used during activation of the dispenser 10. The cover member 18 may be a cardboard or paper-based material in an exemplary embodiment. It is also understood that the dispenser 10 can incorporate a label L, such as on the cover member 18 or the outer container 14.

To fabricate the dispenser, the first chamber 20 of the first container 12 is filled with a desired flowable material M. The open end of the first container 12 through which the flowable material passed to fill the first container 12 is sealed as is known in glass ampoule technology. A sealed glass ampoule 12 having the flowable material M therein is thereby provided (FIG. 3). The filled first container 12 is then inserted through the open first end 36 and into the second chamber 42 of the second container 14. Preferably, the first container 12 is positioned in its entirety within the second chamber 42 of the second container 14. Once the first container 12 is positioned in the second container 14, the applicator assembly 16 is connected to the second container 14. If a filter member is desired, the filter member can be inserted into the open first end 36 of the second container 14 and adjacent one end of the first container 12. As can be appreciated from FIGS. 1-3, an end of the applicator assembly 16 is inserted into the open first end 36 of the second container 14.

It is understood that the dispenser 10 may utilize the cover member 18 in a single-use type container as described above and shown in FIG. 2. The dispenser 10 may also eliminate the cover member 18 and be packaged in other outer packaging such as blister packaging.

The present invention utilizes a dispenser actuator assembly generally designated with the reference numeral 100. The dispenser actuator assembly 100 may also be referred to as an ampoule actuator 100 or dispenser/ampoule holder 100. As explained in greater detail below, the dispenser actuator assembly 100 cooperates with the dispenser 10 to actuate the dispenser 10. The structure of the dispenser actuator assembly 100 will first be described followed by a description of the cooperation and operation of the dispenser actuator assembly 100 with the dispenser 10.

As shown in FIG. 4, the dispenser actuator assembly 100 generally includes a base member 102 and an actuator arm 104. The actuator arm 104 is operably connected to the base member 102 as further described below.

FIGS. 4-8 show the base member 102 of the dispenser actuator assembly 100. The base member 102 is generally an annular member that in one exemplary embodiment is ring-shaped and dimensioned to fit over the glass ampoule assembly as described in greater detail below.

The base member 102 generally includes a central segment 106, a first extending segment 108, a second extending segment 110 and a platform segment 112. In an exemplary embodiment, these segments cooperate to form an annular member or annular ring in certain embodiments. The base member 102 defines an opening therethrough. The central segment 106 is positioned at an upper portion of the base member 102 and generally proximate an end of the actuator arm 104. The first extending segment 108 is a rounded segment and depends from the central segment 106. Similarly, the second extending segment 110 is a rounded segment and depends from the central segment 106. The second extending segment 110 is generally opposite the first extending segment 108. The first extending segment 108 and the second extending segment 110 connect to the platform segment 112, therein completing an annular member. The platform segment 112 has a planar floor member that has a length that extends beyond the central segment 106 and the first extending segment 108 and the second extending segment 110. The first extending segment 108 has a first flared wall portion 114 proximate an end of the segment 108 that connects to the platform segment 112. Similarly, the second extending segment has a second flared wall portion 116 proximate an end of the segment 110 that connects to the platform segment 112. The first flared wall portion 114 has an increasing length or width or dimension towards the platform segment 112 and a decreasing length towards the central segment 106. The second flared wall portion 116 also has an increasing length or width towards the platform segment 112 and a decreasing length towards the central segment 106. The platform segment 112 is dimensioned for a finger or thumb of a user to engage against the platform segment 112 when the user crushes the ampoule 12 to be described. The base member 102 thus forms a cradle to receive the glass ampoule assembly 10 as described in greater detail below. These structures cooperatively define an opening 117 to receive the glass ampoule assembly 10 as described in greater detail below. The opening 117 extends through the base member 102. It is understood that the base member 102 is dimensioned to receive the glass ampoule assembly 10 in a snug-fit or interference type connection wherein the glass ampoule assembly 10 is securely, but removably held in the base member 102.

As shown in FIGS. 4-8, the base member 102 is formed as a full annular member in one exemplary embodiment. The base member 102 is designed to receive or hold the glass ampoule assembly 10, and it is understood that the base member 102 may not have a full ring-shaped configuration. For example, the base member 102 can have certain segments eliminated and not utilized while still having a configuration to receive or hold the glass ampoule assembly 10. The base member 102 could be configured without the platform segment 112. In an alternative embodiment, the platform segment 112 is removed and the first extending segment 108 and the second extending segment 110 are resilient and configured to hold the glass ampoule assembly 10. With the platform segment 112 eliminated, the opening 117 is defined between distal ends of the first extending segment 108 and the second extending segment 110 to receive the glass ampoule assembly 10 therethrough. In a further alternative embodiment, one of the extending segments 108,110 could be configured and dimensioned to removably hold the glass ampoule assembly 10.

FIGS. 4-8 show the actuator arm 104 of the dispenser actuator assembly 100. In one exemplary embodiment, the actuator arm 104 generally includes a central hub 118, a first arm implement 120 and a second arm implement 122. The actuator arm 104 may be considered a first actuator arm 104 as in later embodiments to be described, the actuator assembly 100 utilizes a second actuator arm 104.

The actuator arm 104 has a length and the central hub 118 is positioned between the first arm implement 120 and the second arm implement 122 and generally at a midportion of the actuator arm 104 in an exemplary embodiment. The central hub 118 is further generally aligned with the central segment 106 of the base member 102 as described in greater detail below. In an exemplary embodiment, the central hub 118 is connected to the base member 102 at the central segment 106.

As further shown in FIGS. 4-8, the first arm implement 120 has a proximal end 124 and a distal end 126. The proximal end 124 is connected to the central hub 118 and in an exemplary embodiment, the first arm implement 120 is integral with the central hub 118. The first arm implement 120 has an intermediate segment 128 that has a curvilinear configuration that extends up, above and away from the central hub 118. The curvilinear configuration results in the first arm implement 120 having an curved upper surface and a curved lower surface. As further shown in FIG. 6, the first arm implement 120 has a depending protrusion 130, or first depending protrusion 130, generally at or proximate the distal end 126. The depending protrusion 130 has a contoured surface. The depending protrusion 130 could also take other forms in order to enhance the rupturing capability of the device. As further shown in FIGS. 6-9, the first arm implement 120 has a thumb or finger pad 132 on the outer or upper surface of the first arm implement 120. The finger pad 132 may be in the form of a plurality of ridges although other structural configurations are possible. The depending protrusion 130 is positioned on the first arm implement 120 in a position to enhance crushing of the glass ampoule assembly 10 as will be described in greater detail below.

As further shown in FIGS. 4-8, the second arm implement 122 has a proximal end 134 and a distal end 136. The proximal end 134 is connected to the central hub 118 and in an exemplary embodiment, the second arm implement 122 is integral with the central hub 118. The second arm implement 122 has an intermediate segment 138 that has a curvilinear configuration that extends up, above and away from the central hub 118. The curvilinear configuration results in the second arm implement 122 having an curved upper surface and a curved lower surface. As further shown in FIG. 4-8, the second arm implement 122 has a depending protrusion 140, or second depending protrusion 140, generally at or proximate the distal end 136. The depending protrusion 140 has a contoured surface. The depending protrusion 140 could also take other forms in order to enhance the rupturing capability of the device or the ability to manipulate the dispenser held by the dispenser actuator assembly 100. As further shown in FIG. 4-8, the second arm implement 122 has a thumb or finger pad 142 on the outer or upper surface of the second arm implement 122. The finger pad 142 may be in the form of a plurality of ridges although other structural configurations are possible. The depending protrusion 140 is positioned on the second arm implement 122 in a position to enhance crush and/or manipulation of the glass ampoule assembly 10 as will be described in greater detail below.

As discussed, the actuator arm 104 is connected to the base member 102 wherein the first arm implement 120 and the second arm implement 122 are connected to the base member 102. In one exemplary embodiment, the central hub 118 of the actuator arm 104 is generally connected to the central segment 106 of the base member 102. In exemplary embodiments, the actuator arm 104 is integral with the base member 102. FIGS. 6 and 8 show additional structures associated with the actuator arm 104 and base member 102. As described in greater detail below, the actuator arm 104, including the first arm implement 120 and the second arm implement 122 are resiliently flexible. A first hinge 144 is defined proximate the proximal end 124 of the first arm implement 120 and the central hub 118 and the central segment 106 of the base member 102. The first hinge 144 defines a first cut-out portion 146 that extends into the actuator arm 104. The first cut-out portion 146 may be considered to have inclined surfaces defining a v-shape although the cut-out portion 146 can include other configurations. A second hinge 148 is defined proximate the proximal end 134 of the second arm implement 122 and the central hub 118 and the central segment 106 of the base member 102. The second hinge 148 defines a second cut-out portion 150 that extends into the actuator arm 104. The second cut-out portion 150 may be considered to have inclined surfaces defining a v-shape although the cut-out portion 148 can include other configurations. The hinges 144,148 assist in the pivoting and deflecting of the first arm implement 120 and the second arm implement 122 with respect to the base member 102 as will be described in greater detail below. The cut-out portions 146,150 of the hinges 144,148 can have different shapes such as a v-notch or a more contoured cut-out portion. It is understood that the hinges 144,148 can be structured differently wherein the respective arm implements 120,122 deflect differently based on the desired function of the actuator assembly 100.

The dispenser actuator assembly 100 is used with a dispenser 10 such as a glass ampoule assembly 10 to crush the glass ampoule assembly 10 and dispense flowable material from the glass ampoule assembly 10. As shown in FIG. 8, the glass ampoule assembly 10 is prepared such as by removing the cardboard sleeve 18 if the sleeve 18 is being used or removing the glass ampoule assembly 10 from any blister packaging. The glass ampoule assembly 10 is inserted into the base member 102. The opening 117 defined by the cooperating segments of the base member 102 receives the glass ampoule assembly 10 wherein the base member 102 slides onto the second container 14. In one exemplary embodiment, the base member 102 slides onto the second container 14 in a frictional interference fit. The annular ring of the base member 102 is dimensioned to fit circumjacently around the glass ampoule assembly 10 in an interference fit. It is understood that the one of the dispenser actuator assembly 100 and the glass ampoule assembly 10 could have a locating structure thereon to properly position the dispenser actuator assembly 100 on the glass ampoule assembly 10 so that the actuator arm 104 is properly positioned to crush the glass ampoule 12. The location structure can also take the form of a cooperative structure on one of or both of the dispenser actuator assembly 100 and the glass ampoule assembly 10. For example, the second container 14 of the glass ampoule assembly 10 could have an annular, radially-inwardly formed indentation that the base member 102 is received therein to automatically locate the dispenser actuator assembly 100 on the proper location on the glass ampoule assembly 10. Similarly, an outwardly extending protrusion could be located on the second container wherein the base member 102 slides over the protrusion until the actuator assembly 100 fits adjacent the protrusion to be properly located. Multiple protrusions could also be used such as outwardly extending spaced protrusions wherein the actuator assembly 100 fits within spaced protrusions to be properly located. FIGS. 3-4 show another location structure wherein the dispenser actuator assembly 100 has protrusions 121 at the platform segment 112 and central segment that cooperate with indentations 15 on the second container 14.

Figure 9:
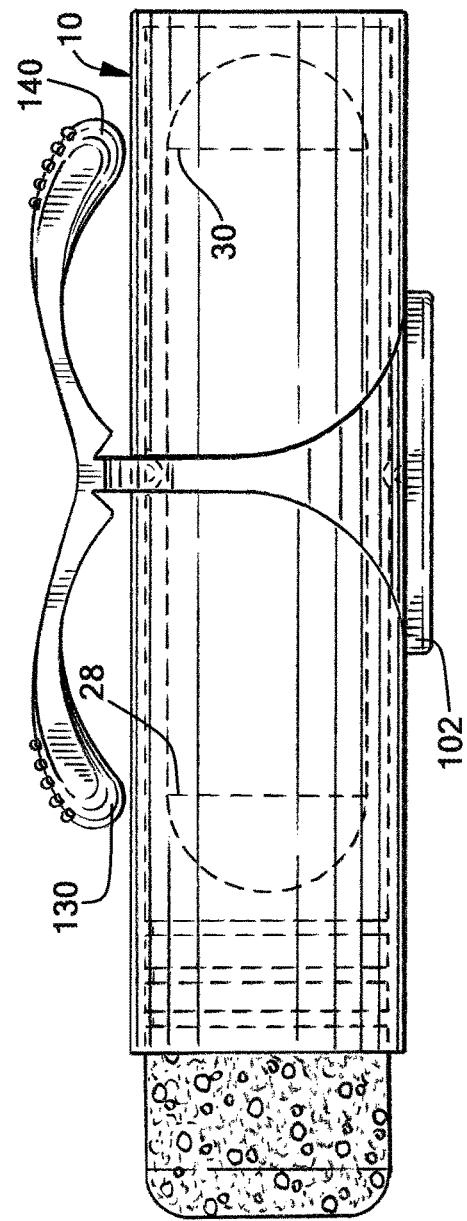
FIG. 9 is a side elevation view of the dispenser actuator assembly mounted on the glass ampoule assembly and positioned to crush a glass ampoule of the glass ampoule assembly.

FIG. 8 shows the dispenser actuator assembly 100 positioned on and operably connected to the glass ampoule assembly 10. It is understood that dispenser actuator assembly 100 can be slidably moveable along the glass ampoule assembly 10, which feature applies to other embodiments described herein. The glass ampoule assembly 10 is now ready to be actuated. The first container 12, or glass ampoule 12, is in a position to be crushed wherein the flowable material M can be dispensed from the assembly 10. As shown in FIGS. 8 and 9, in a first neutral position, the first arm implement 120 is positioned such that the implement 20 extends along the second container 14 wherein the first protrusion 130 is positioned proximate the first interface area 28 of the glass ampoule 12. Similarly, in a second neutral position, the second arm implement 122 is positioned such that the implement 122 extends along the second container 14 wherein the second protrusion 140 is positioned proximate the second interface area 30 of the glass ampoule 12. As further shown in FIG. 9, the first depending protrusion 130 is spaced from the second container 14 and positioned over and proximate the first interface area 28. Similarly, the second depending protrusion 140 is spaced from the second container 14 and positioned over and proximate the second interface area 30.

Figure 10:
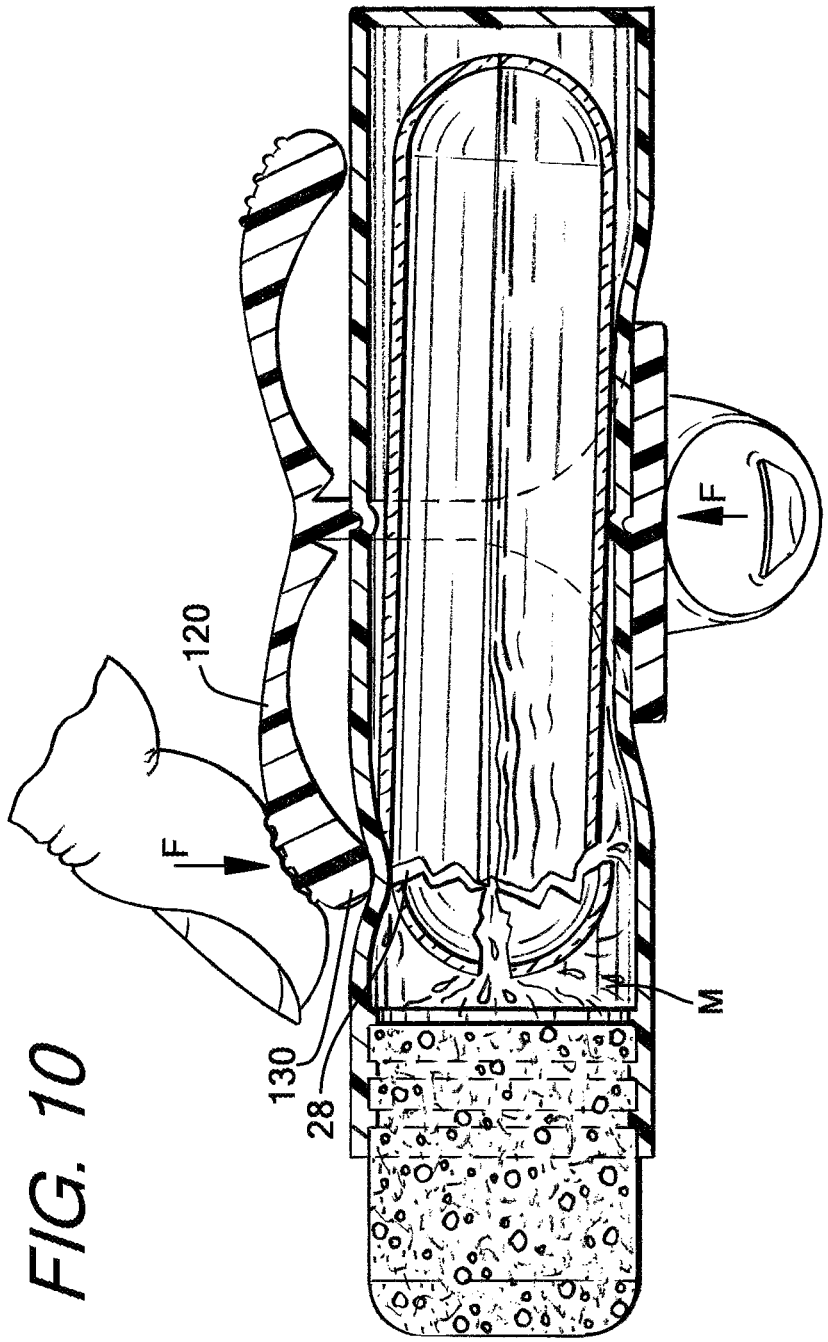
FIG. 10 is a side cross-sectional view of the dispenser actuator assembly mounted on the glass ampoule assembly and showing a user actuating the actuator assembly to crush the glass ampoule of the glass ampoule assembly.
Figure 11:
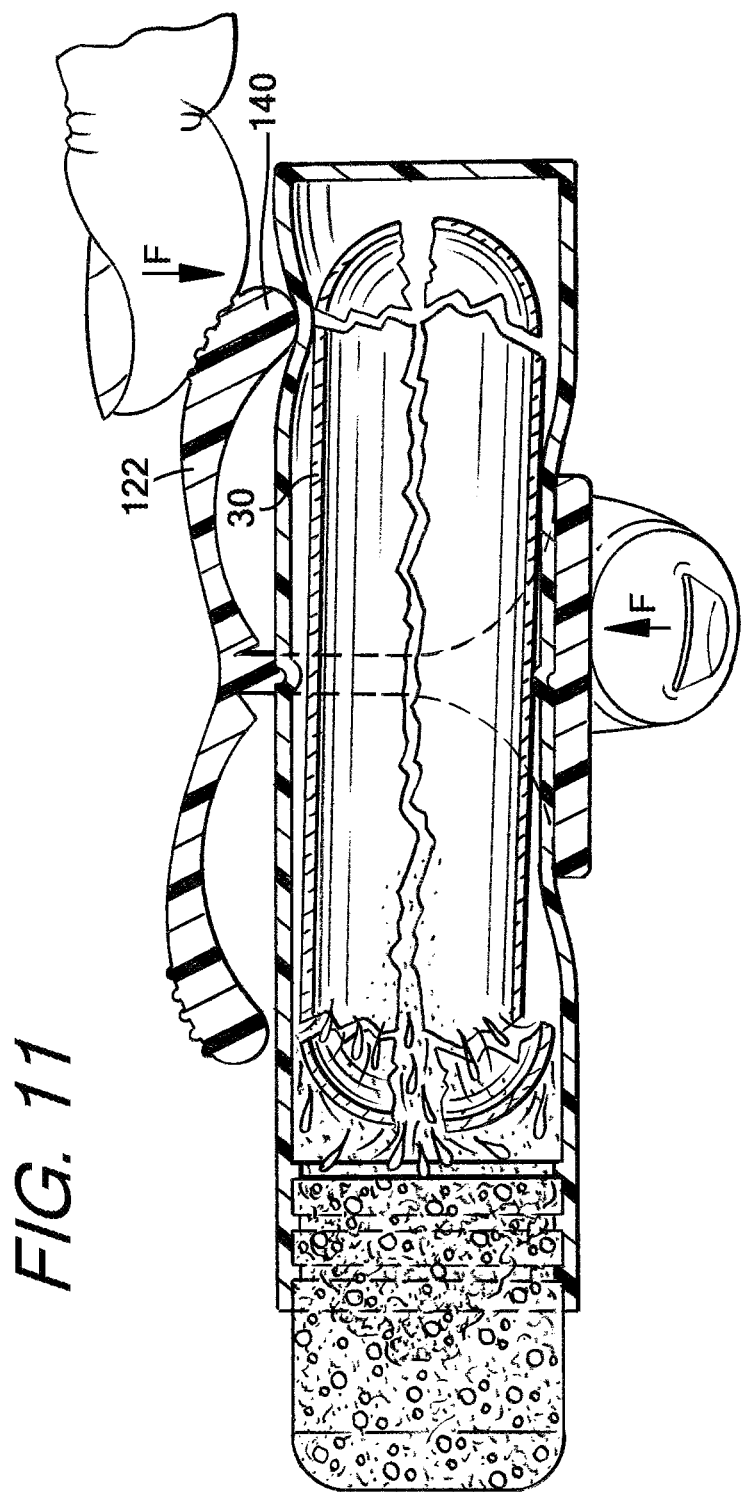
FIG. 11 is a side cross-sectional view of the dispenser actuator assembly mounted on the glass ampoule assembly and showing the user further actuating the actuator assembly to force flowable material from the glass ampoule assembly.
Figure 12:
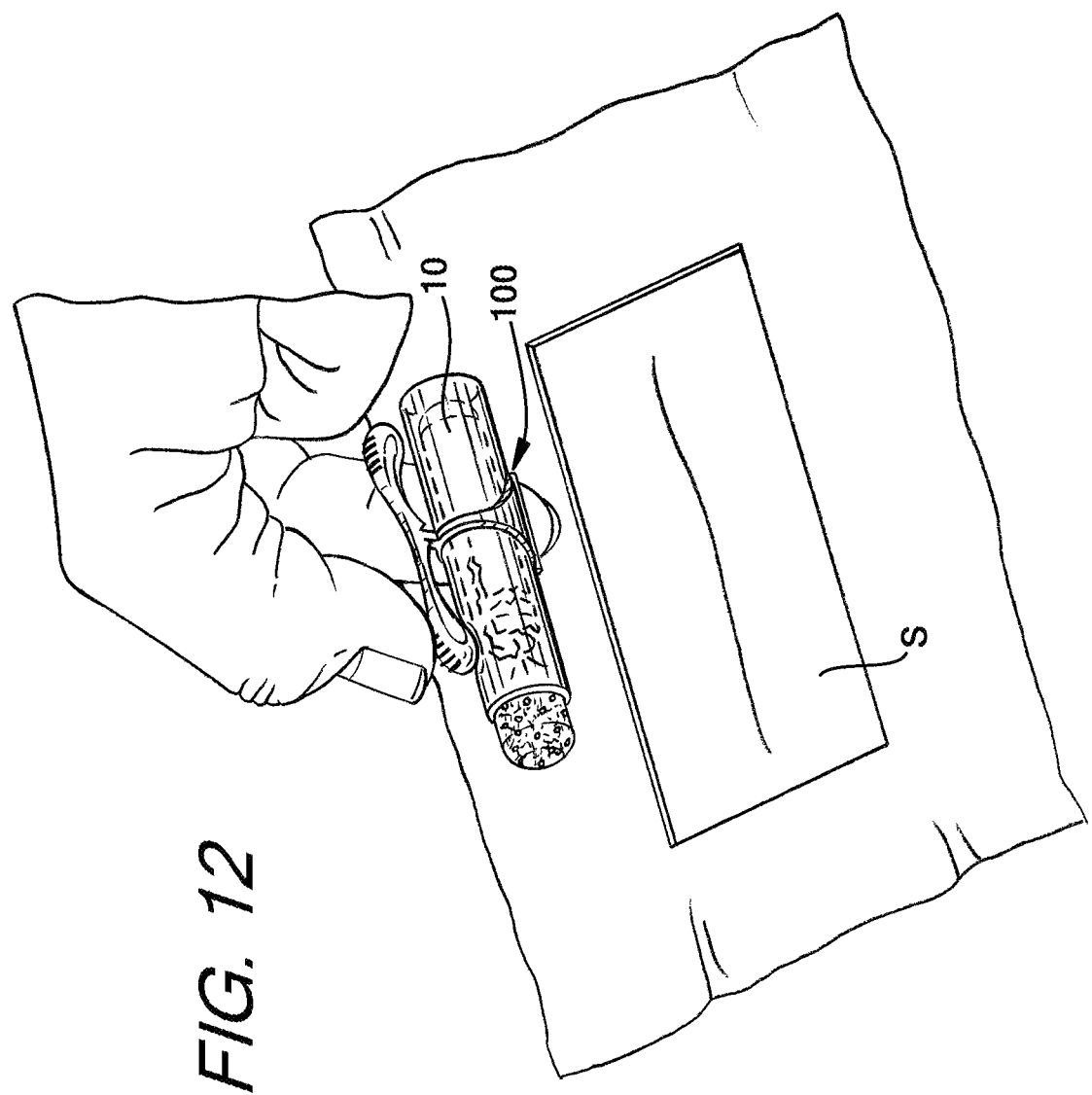
FIG. 12 is a perspective view of a user actuating the dispenser actuator assembly to crush the glass ampoule similar to as shown in FIG. 10.
Figure 13:
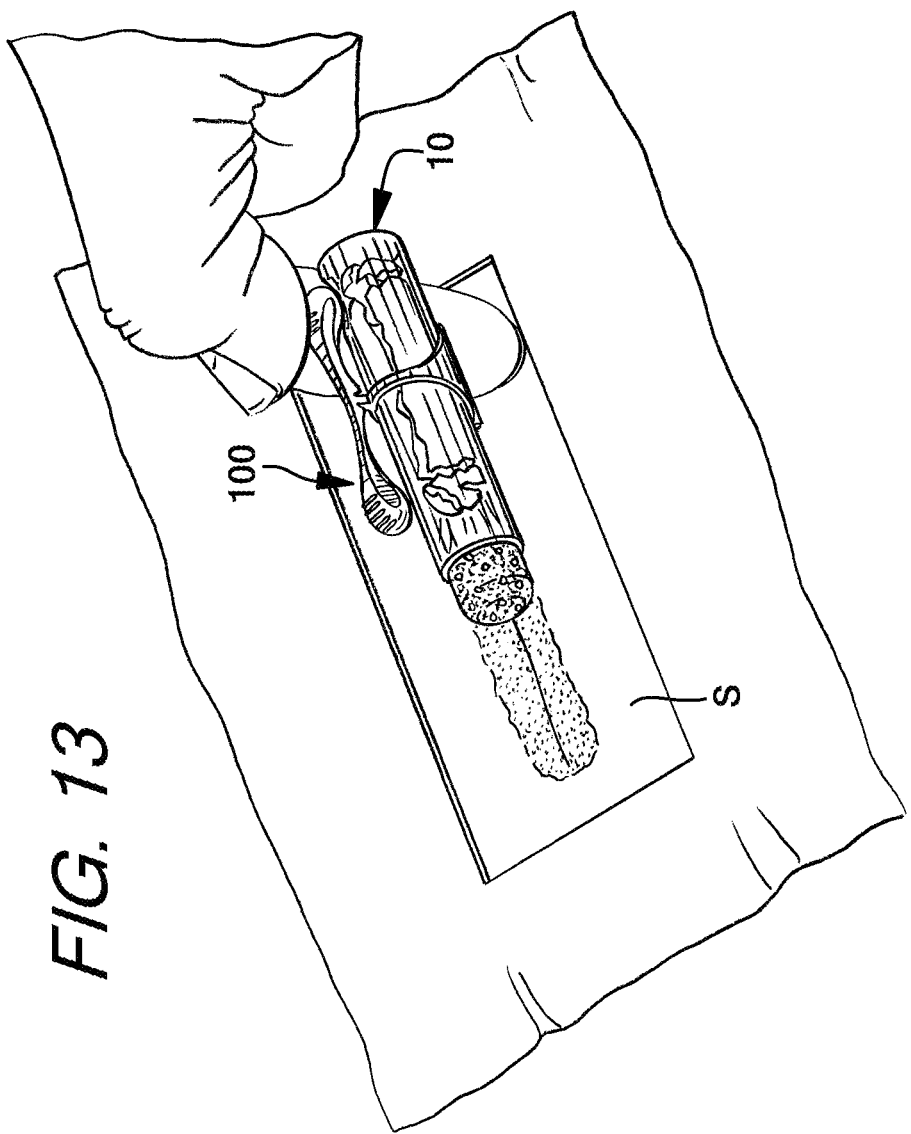
FIG. 13 is a perspective view of a user manipulating the dispenser actuator assembly to force flowable material from the glass ampoule assembly and onto a receiving surface similar to as shown in FIG. 11.

A user holds the dispenser actuator assembly 100 wherein a forefinger wraps around an underside of the base member 102 and engages an exterior of the platform segment 112 as shown in FIG. 10. A thumb of the user engages the finger pad 132 of the first arm implement 120. The user squeezes the actuator assembly 100 thereby applying a compressive force F wherein the first depending protrusion 130 is deflected towards and engages the second container 14. Thus, the first arm implement 120 is pivotable about the first hinge 144 from the first neutral position to a first actuating position. The forefinger of the user supplies a resistive force opposite to the force applied by the thumb of the user. In this fashion, it is understood that the compressive force F is applied at offset locations on the actuator assembly 100 and glass ampoule assembly 10. As the user continues to depress the first arm implement 120, the first depending protrusion 130 deflects the second container 14 wherein the second container 14 engages the glass ampoule 12 at proximate the first interface area 28 wherein the glass ampoule 12 is crushed. Upon being crushed, the flowable material M passes from the glass ampoule 12 and into the applicator 16. Because force F is applied to the glass ampoule 12 at the first interface area 28, the domed portion of the glass ampoule 12 breaks into multiple pieces allowing enhanced flow of the flowable material M out of the glass ampoule 12 and into the second container 14 and to the applicator assembly 16. It has been determined by the inventors that if the glass ampoule 12 is crushed at the interface area, the domed-section will break into multiple pieces rather than remaining intact while breaking away from the intermediate section of the glass ampoule 12. As shown in FIG. 10, the flowable material M passes from the second container 14 and into the applicator assembly 16. As further shown in FIG. 11, the user can also engage the second arm implement 122 at the second finger pad 142. Thus, the second arm implement 122 is pivotable about the second hinge 148 from the second neutral position to a second actuating position A thumb of the user engages the second finger pad 142 of the second arm implement 122. The user squeezes the actuator assembly 100 thereby applying a compressive force F wherein the second depending protrusion 140 is deflected towards and engages the second container 14. As the user continues to depress the second arm implement 122, the second depending protrusion 140 deflects the second container 14 wherein the second container 14 engages the glass ampoule 12 at proximate the second interface area 30 wherein the glass ampoule 12 is further crushed. Upon this additional crushing, the flowable material M more easily passes from the glass ampoule 12 and into the second container 14 and into the applicator 16. Because force is applied to the glass ampoule 12 at the second interface area 30, the domed portion of the glass ampoule 12 breaks into multiple pieces allowing enhanced flow of the flowable material M out of the glass ampoule 12 and into the second container 14 and to the applicator assembly 16. It is further understood that the user can use the second arm implement 122 to further deflect and manipulate the second container 14 and force the flowable material M through the applicator assembly 16 and, therefore, to enhance dispensing of the flowable material M from the glass ampoule assembly 10. It is understood that the applicator assembly 16 assists in minimizing the chance of glass shards from the crushed glass ampoule 12 from passing out of the glass ampoule assembly 10. In addition, the outer wall of the second container 14 prevents glass shards from cutting fingers of the user thereby protecting the user's fingers from injury by the fractionated glass shards of the glass ampoule 12 that remain in the second container 14. Because a user engages the actuator assembly 100 to crush the glass ampoule assembly 10 rather than engaging the glass ampoule assembly 10 directly, the chance of cutting a user's fingers/thumb from glass shards is further minimized. It is understood that additional structures could be incorporated into the glass ampoule assembly 10 such as filter assemblies to minimize the chance of glass shards from passing through the applicator assembly. As shown in FIGS. 12 and 13, the flowable material M can be dispensed from the glass ampoule assembly 10 and onto a receiving surface S. The receiving surface S can vary depending the particular type of flowable material M being dispensed. From the above operational description, it is understood that the first arm implement 120 is pivotable independently of the pivoting of the second arm implement 122.

Figure 14:
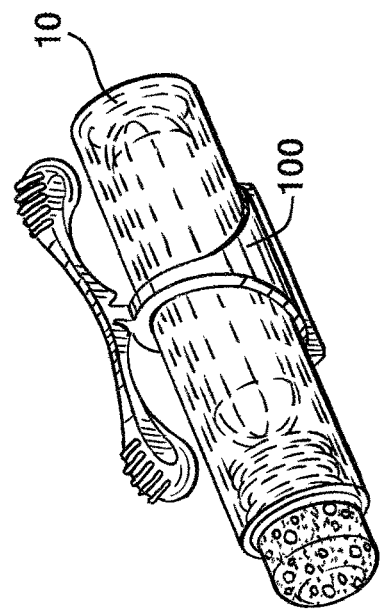
FIG. 14 is a perspective view of the dispenser actuator assembly capable of being reused with a new glass ampoule assembly.

As discussed above and shown in FIGS. 12-14, the user dispenses the flowable material M from the glass ampoule assembly 10 with the aid of the dispenser actuator assembly 10. Once the flowable material M is emptied from the glass ampoule assembly 10, the dispenser actuator assembly 100 can be removed from the glass ampoule assembly 10. In this fashion, the dispenser actuator assembly 10 can be reused with multiple glass ampoule assemblies as shown in FIG. 14 where the actuator assembly 100 is mounted on a new ampoule assembly 10. In this configuration, the dispenser actuator assembly can be formed from a more robust and higher-cost material. In other configurations, the material used to form the dispenser actuator assembly 100 could be a lower cost material that is designed as a one-time use wherein the dispenser actuator assembly 100 is disposable. In such case, the location structured used to position the dispenser actuator assembly 100 on the glass ampoule assembly 10 could be structured to permanently attach the dispenser actuator assembly 100 to the glass ampoule assembly 10. Once the flowable material M is fully dispensed from the glass ampoule assembly, the attached structures can be simply discarded together.

Figure 15:
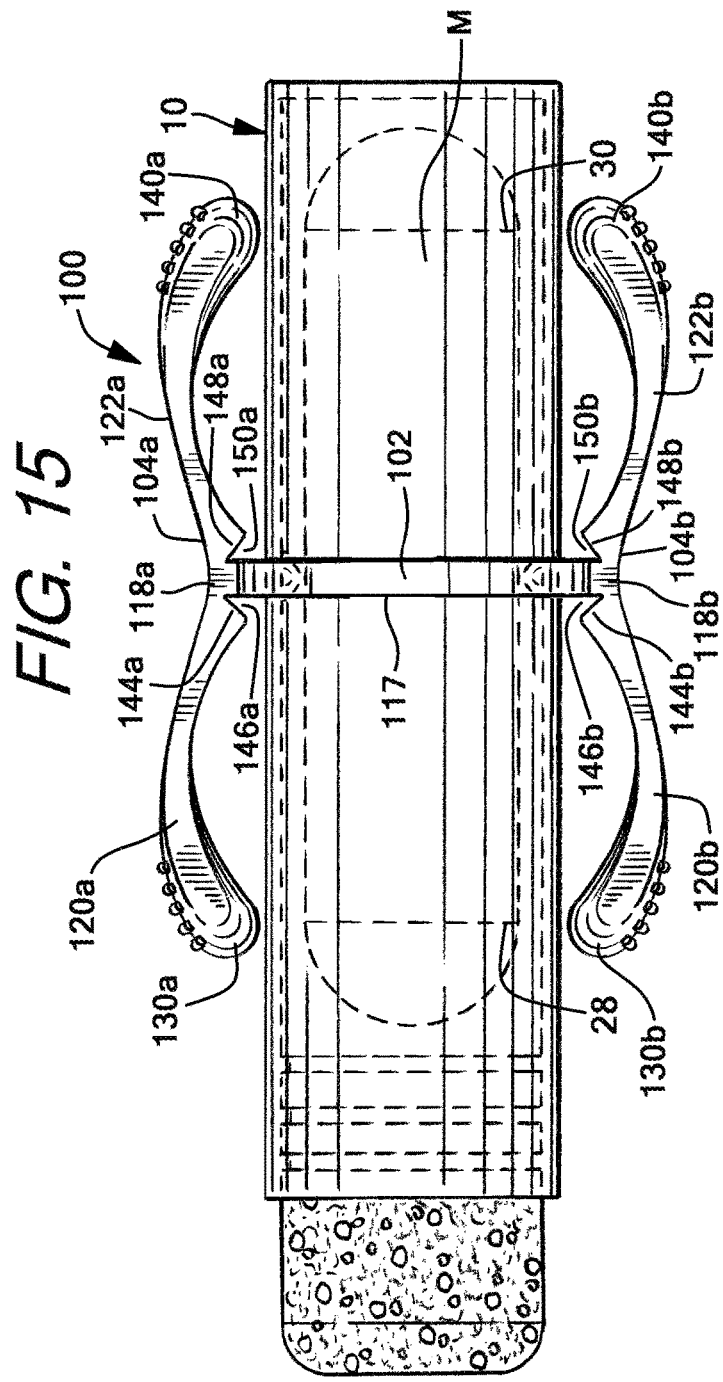
FIG. 15 is a side elevation view of an alternative embodiment of the dispenser actuator assembly mounted on a glass ampoule assembly.

FIG. 15 discloses another embodiment of the dispenser actuator assembly of the present invention. In this embodiment, the dispenser actuator assembly is designated with the reference numeral 100 and utilizes a pair of actuator arms rather than a single actuator arm. Similar structures will be referenced with similar reference numerals used in described the above embodiments and the actuator arms will be designated in an "a" series and a "b" series.

As further shown in FIG. 15, the dispenser actuator assembly 100 has a base member 102 and an actuator arm 104. The base member 102 generally takes the form of an annular ring member wherein the platform segment is not utilized as in the previous embodiment. The base annular ring member defines an opening 117. In this particular embodiment, the actuator arm 104 comprises a first actuator arm 104a and a second actuator arm 104b. Similar to the embodiment of FIGS. 1-14, the first actuator arm 104a has a first arm implement 120a and a second arm implement 122a that extend from a central hub 118a of the first actuator arm 104a. The first arm implement 120a has a depending protrusion 130a, and the second arm implement 122a has a depending protrusion 140a. Similar to the previous embodiment, a first hinge 144a is defined by a first cut-out portion 146a and a second hinge 148a is defined by a second cut-out portion 150a. The second actuator arm 104b has a first arm implement 120b and a second arm implement 122b that extend from a central hub 118b of the second actuator arm 104b. The first arm implement 120b has a first depending protrusion 130b, and the second arm implement 122b has a second depending protrusion 140b. Similar to the previous embodiment, a first hinge 144b is defined by a first cut-out portion 146b and a second hinge 148b is defined by a second cut-out portion 150b. As further shown in FIG. 15, the actuator arms 104a,104b, associated implements 120a,120b, 122a, 122b and depending protrusions 130a,130b,140a, 140b are dimensioned to be positioned proximate the interface areas 28,30 of the glass ampoule 12.

As can be further appreciated from FIG. 15, in operation, a user can engage the respective first arm implements 120a,120b of the first actuator arm 104a and the second actuator arm 104b to crush the glass ampoule at the first interface area 28. The user can also engage the respective second arm implements 122a,122b of the first actuator arm 104a and the second actuator arm 104b to crush the glass ampoule at the second interface area 30. The flowable material contained in the glass ampoule 12 can pass to the applicator 16 to be dispensed from the dispenser 10.

FIG. 16 discloses another embodiment of the ampoule actuator assembly 100 of the present invention. The ampoule actuator assembly has a base member 102 and an actuator arm having a first arm implement and a second arm implement. Other structures described above are also incorporated into the ampoule actuator assembly of FIG. 16. The glass ampoule assembly utilized in FIG. 16 is a tandem-type ampoule assembly wherein a first glass ampoule 12 and a second glass ampoule 12 are contained in the outer container 14. The first glass ampoule contains a first flowable material M1 and the second glass ampoule contains a second flowable material M2. The base member of the ampoule actuator assembly is mounted on the tandem glass ampoule assembly similar to the previous embodiments. In operation, a user engages the first arm implement 120 to engage and deflect the outer container to crush the first glass ampoule 12. The user also engages the second arm implement 122 to engage and deflect the outer container 14 to crush the second glass ampoule 12. The first flowable material M1 mixes with the second flowable material M2 to form a mixture MX. The applicator receives the mixture MX to be dispensed from the tandem glass ampoule assembly. It is understood that the length of the first arm implement 120 and the second arm implement 122 can vary in length as desired. In an exemplary embodiment, the arm implements 120,122 may be dimensioned such that the associated depending protrusion may be positioned proximate an interface area of the glass ampoule wherein the glass ampoules are crushed at the interface areas 28,30.

FIG. 17 discloses another embodiment of the ampoule actuator assembly 100 of the present invention. A tandem glass ampoule assembly is also utilized in this embodiment as in FIG. 16. The ampoule actuator assembly 100 utilizes a first actuator arm 104a and a second actuator arm 104b. Operation of the ampoule actuator assembly of FIG. 17 is similar as described with respect to the ampoule actuator assembly of FIG. 15 utilizing a first actuator arm 104a and a second actuator arm 104b. The ampoule actuator assembly 100 of FIG. 17 utilizes other structures such as the hinges 144,148 and the descriptions above apply to this embodiment as well.

FIG. 18 discloses another embodiment of the dispenser actuator assembly 100 of the present invention. The dispenser actuator assembly is similar to the embodiment shown in FIG. 16. The glass ampoule assembly is a tandem glass ampoule assembly. The outer container 14, has a dividing wall 15 that defines a first chamber 42a having a first open end and a second chamber 42b having a second open end. The first glass ampoule 12a is received in the first chamber and the second glass ampoule 12b is received in the second chamber. The first glass ampoule 12a has a first flowable material M1, and the second glass ampoule 12b has a second flowable material M2. A first applicator 16a is received in the first open end and a second applicator 16b is received in the second open end. The glass ampoules are crushed as described above regarding the previous embodiments via the first arm implement 120 and the second arm implement 122. This embodiment is useful in applications where multiple flowable materials are in use but that are to be separately dispensed from the glass ampoule assembly. It is understood that the dispenser actuator assembly 100 can slidably move along the outer container 14 and crush the glass ampoules 12a,12b at desired locations.

FIG. 19 discloses another embodiment of the dispenser actuator assembly 100 of the present invention. This embodiment also utilizes the glass ampoule assembly having an outer container having a dividing wall 15 as described in FIG. 18. The dispenser actuator assembly is similar in structure as shown in FIG. 17. Similar to the operation described in FIGS. 17 and 18, the first glass ampoule 12a and the second glass ampoule 12b can be crushed by the respective implements of the first actuator arm 104z and the second actuator arm 104b. The flowable materials M1,M2 can be dispensed from the respective applicators 16a, 16b.

FIG. 20 shows another dispenser 10 in the form of a plastic ampoule 10 having an outer wall 50 and a rupturable membrane 52 defining a chamber 54 for containing a flowable material M. The membrane 52 has a weld seam 56 formed during an injection molding process wherein a first segment of injected molding material abuts a second segment of injected molding material to form the weld seam 56 such as disclosed in U.S. Pat. No. 6,641,319, which patent is expressly incorporated herein by reference. Similar to the operation described above, after the dispenser actuator assembly 100 is mounted on the plastic ampoule 10, a user applies a compressive force F to the first arm implement of the actuator arm wherein the protrusion engages and deflects the outer wall 50 of the plastic ampoule 10 thereby applying the force proximate the membrane 52 wherein the weld seam 56 is fractured. Upon fracturing of the weld seam 56, the flowable material M can pass through the membrane 52 and into the applicator 16 to be dispensed from the plastic ampoule 10. It is understood that the protrusion 130 is positioned proximate the membrane 52 to apply the force to the membrane 52 to rupture the weld seam 56. It is further understood that the second protrusion 140 is positioned proximate the first chamber 54 to assist in manipulating the flowable material from the dispenser 10. FIG. 21 shows another dispenser 10 in the form of plastic ampoule 10 similar to the plastic ampoule shown in FIG. 20. The plastic ampoule 10 shown in FIG. 21 has an angled or conical membrane such as disclosed in U.S. Pat. No. 10,392,163, which patent is expressly incorporated herein by reference. Operation of fracturing the conical membrane in FIG. 21 is similar to FIG. 20 and the above descriptions apply to the embodiment of FIG. 21.

Figure 22:
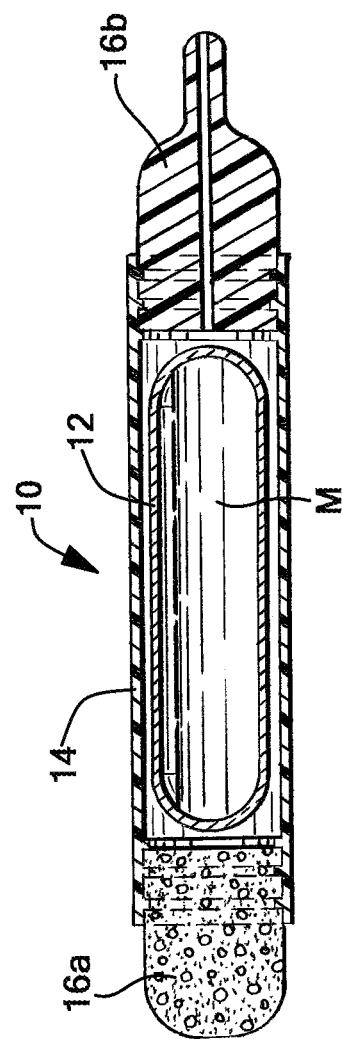
FIG. 22 is a side cross-sectional view of an alternative embodiment of a dispenser in the form of a glass ampoule assembly having multiple applicators including a swab and a dropper applicator.
Figure 23:
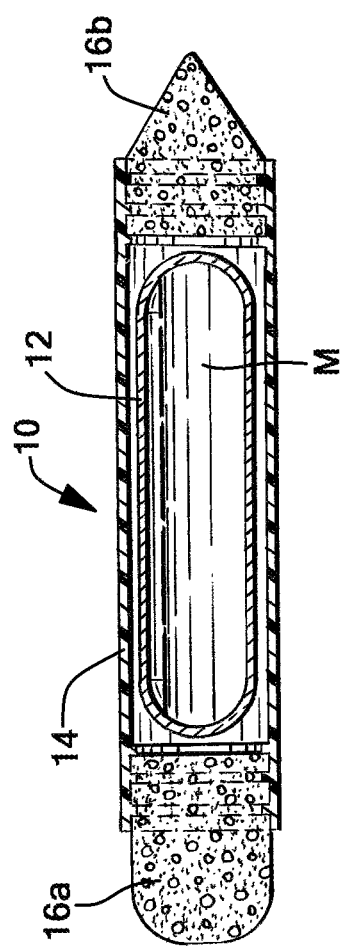
FIG. 23 is side cross-sectional view of an alternative embodiment of a dispenser in the form of a glass ampoule assembly having multiple applicators including different swab applicators.

FIG. 23 discloses another alternative embodiment of the present invention in the form of an alternative dispenser 10. The dispenser 10 is a glass ampoule assembly 10 as described above. The outer container 14 has two open ends wherein one end receives a first applicator 16a and an opposite end receives a second applicator 16b. The first applicator 16a and the second applicator 16b have different structures and characteristics for dispensing the flowable material M based on desired results or application. For example, the first applicator 16a may have a larger flatter tip to dispense flowable material in a general manner. The first applicator 16a is a swab assembly may have a generally constant diameter along a length of the swab assembly. The second applicator 16b is a swab assembly that has a tapered structure to define a more narrow tip to dispense the flowable material M in a more precise manner where necessary. The second applicator 16a is tapered along the length of the second swab assembly wherein the swab tapers to have an apex at a distal end. The user can decide which applicator 16a,16b to use based on the need of the application. FIG. 22 discloses yet another alternative embodiment of the present invention, similar to the glass ampoule assembly 10 shown in FIG. 23. The glass ampoule assembly 10 utilizes multiple applicators 16. In this exemplary embodiment, the first applicator 16a is a swab assembly 16a, while the second applicator 16b is a dropper assembly 16b. After crushing the glass ampoule 12, the user can dispense the flowable material M through the swab 16a or the dropper assembly 16b.

FIG. 24 discloses another alternative embodiment of the present invention. The alternative dispenser 10 is in the form of two plastic ampoules. Similar to the plastic ampoule described in FIG. 20, each plastic ampoule 10 has an outer wall 50 and a rupturable membrane 52 defining a chamber 54 for containing a flowable material M. The membrane 52 has a weld seam 56 formed during an injection molding process wherein a first segment of injected molding material abuts a second segment of injected molding material to form the weld seam 56 such as disclosed in U.S. Pat. No. 6,641,319, which patent is expressly incorporated herein. Each plastic ampoule contains a flowable material M to be dispensed. The first plastic ampoule may have a first flowable material M1, and the second plastic ampoule may have a second flowable material M2. In one exemplary embodiment, the first plastic ampoule may have a generally circular cross-section, or circular and cylindrical configuration and the second plastic ampoule may have a generally circular cross-section or circular and cylindrical configuration. The respective sizes and dimensions of the cross-section may coincide or be identically sized wherein the ends of the plastic ampoules can be placed in confronting relation and surface-to-surface contact. As further shown in FIG. 22, ends of the plastic ampoules 10 are connected together at a connection area 60 to form a tandem plastic ampoule assembly 10. The connection of the plastic ampoules 10 can take various forms. The connection may be an adhesive connection or other sealant type connection. In one exemplary embodiment, the ends of the plastic ampoules 10 are spin welded together to form a spin weld 62 wherein the plastic ampoules 10 form a single unit. With such connection, the first plastic ampoule and the second plastic ampoule extend away from each other linearly along a longitudinal axis L. The respective applicators 16 are at opposite distal ends from one another. In such configuration, the tandem plastic ampoule can contain different flowable materials M and used in applications where the different flowable materials M1,M2 are needed to be separately stored and dispensed in a consecutive manner. FIG. 25 shows a further alternative embodiment similar to the embodiment of FIG. 24. In this embodiment, the plastic ampoules 10 utilize the angled or conical membrane as described above. Consistent with the discussions above, it is understood that the dispenser actuator assembly 100, including the various embodiments, may be used with the tandem dispensers of FIGS. 24-25 to fracture the membranes 52.

The actuator arms of the dispenser actuator assembly can vary in structure as needed for various applications. For example, the length of the actuator arm can vary depending on a length of a glass ampoule for the depending protrusion to be aligned proximate the interface area of the glass ampoule. It is understood that the dispenser actuator assembly is made in an injection molding process to form a unitary structure. A two-shot molding process can be used wherein one of the arm implements could be more flexible than the other arm implement and vice versa.

The dispenser actuator assembly 100 provides several benefits. The actuator assembly provides mechanical advantage for a user to rupture or fracture the dispenser. The dispenser actuator assembly is designed to crush the glass ampoule at the optimal location at the interface area proximate the domed-portion of the glass ampoule to enhance the rupturing of the glass ampoule. Furthermore, as the user engages the actuator arms of the assembly rather than directly engaging the outer container of the dispenser, the chances that glass shards from the crushed glass ampoule can injure the fingers or hand of the user is minimized. The actuator arms can also vary in length and resiliency to provide a desired mechanical force in rupturing the dispenser. Because the dispenser actuator assembly allows for a user to apply an increased force than from finger pressure alone, the assembly can be used to rupture more robustly designed dispensers. Such dispensers may be designed to rupture under an increased force to minimize the chances of inadvertent rupture. In addition, the dispenser actuator assembly 100 can be removable attached to the dispenser. Once the dispenser is ruptured and the flowable material is dispensed from the dispenser, the dispenser actuator assembly can be removed from the dispenser and used to rupture multiple other dispensers. It is understood as well that the dispenser actuator assembly could be manufactured as a single-use assembly that is discarded.

It is understood that any reference to an element using designations such as "first" or "second" or the like does not limit the quantity or order of those elements, unless such limitation is explicitly stated. These designations are used to distinguish between elements or other references to an element. Accordingly, a reference to a first element or a second element does not mean that only two elements may be employed or that the first element must precede the second element in some manner. In addition, a set of elements may comprise one or more elements. In addition, references to "top" or "bottom" or "front" or "rear" are used to reference relative positions of elements and should be construed as a limiting positional requirement.

It is further understood that the present description includes several different embodiments with different features depending on the embodiment being described. It is understood that the various features or structures can be combined among the various embodiments in further exemplary embodiments of the invention.

The dispenser 10 is permitted to be used in a wide variety of uses and applications, and contain and dispense a large variety of fluids and other flowable substances. The following is a non-exhaustive discussion regarding the many possible uses for the dispenser of the present invention, and in particular, the types of materials that are capable of being contained in the dispensers and dispensed therefrom. It is understood that related uses to those described below are also possible with the dispenser. It is also understood that the following discussion of potential uses is applicable to any of the dispenser embodiments disclosed and discussed herein.

The dispenser used with the dispenser actuator assembly of the present invention is designed to primarily contain and dispense flowable materials that are fluids. Other flowable materials can also be dispensed. For example, the flowable material could be a liquid, powder, gel or other type of flowable substance or flowable material. Also, in other embodiments such as dispensers containing multiple chambers for different flowable materials, the flowable materials M1, M2 could both be fluids. In another embodiment, the first flowable material M1 could be a liquid, and the second flowable material M2 could be a powder to be mixed with the fluid. Other combinations depending on the use are also permissible.

This permits the dispenser 10 to be used in a wide variety of uses and applications, and contain and dispense a large variety of fluids and other flowable substances. The following is a non-exhaustive discussion regarding the many possible uses for the dispenser of the present invention, and in particular, the types of materials that are capable of being contained in the dispensers and dispensed therefrom. It is understood that related uses to those described below are also possible with the dispenser. It is also understood that the following discussion of potential uses is applicable to any of the dispenser embodiments disclosed and discussed herein.

In one example, the dispenser of the present invention can be used in medical applications. In one particular exemplary embodiment, the dispenser may contain a surgical antiseptic such as for cleaning and preparing a body area for incision, and sometimes referred to as a surgical prep solution. One type of antiseptic may be chlorhexidine gluconate (CHG). This CHG-based antiseptic could also be combined with a medical sealant such as cyano-acrylic wherein the dispenser is used to contain and dispense cyano-acrylic chlorohexidine gluconate (CACHG). Other types of medical sealants could also be used. Other types of antiseptics could be iodine-based such as iodophoric skin tinctures, which are commercially available. Other antiseptics and antimicrobial agents could also include other iodine-based complexes, alcohol-based complexes or peroxides. Additional additives may also be used with the antiseptic such as colorants. A single chamber dispenser may be used in such an application, but a multi-chamber dispenser such as disclosed herein may also be used.

In another example, the dispenser of the present invention can be used in adhesive-type applications. The dispenser can dispense a flowable material or mixture that is an adhesive, epoxy, or sealant, such as an epoxy adhesive, craft glue, non-medical super glue and medical super glue. The dispenser could also be used with shoe glue, ceramic epoxy and formica repair glue. The dispenser could further be used for a variety of other adhesive dispensing applications, mastic-related resins or the like.

In another example, the dispenser of the present invention can be used in automotive applications. The dispenser can dispense a flowable material or mixture that is an automotive product, such as a rear view mirror repair kit, a vinyl repair kit, auto paints, an auto paint touch up kit, a window replacement kit, a scent or air freshener, a windshield wiper blade cleaner, a lock de-icer, a lock lubricant, a liquid car wax, a rubbing compound, a paint scratch remover, a glass/mirror scratch remover, oils, radiator stop-leak, a penetrating oil, or a tire repair patch adhesive. Other automotive applications could include acetone-based products such as windshield primer. Additional automotive applications could be for general auto/motorcycle or bicycle repair kits including chain oils.

In another example, the dispenser of the present invention can be used in chemistry-related applications. The dispenser can dispense a flowable material or mixture that is a chemistry material such as a laboratory chemical, a buffer solution, a rehydration solution of bacteria, a biological stain, or a rooting hormone. The dispenser may also be used as a chemical tester. In one such application, the dispenser can be used for testing drinks for various "date rape" drugs. Other types of chemical testers are also possible. The dispenser could be used to contain various types of chemicals including solvents. In a particular application, the additional material formulations used to form the dispenser allow the dispenser to store and dispense methyl ethyl ketone.

In another example, the dispenser of the present invention can be used to dispense a flowable material or mixture is a cosmetic and beauty supply/toiletry product. For example, the dispenser can be used for a nail polish, lip gloss, body cream, body gel, body paints, hand sanitizer, nail polish remover, liquid soaps, skin moisturizers, skin peels, tooth whiteners, hotel samples, mineral oils, toothpastes, mouthwash or sunscreens. The flowable material could also be a fragrance such as women's perfume or men's cologne. The flowable material could also be tattoo inks. The flowable material could be used for solutions for treating and/or removing tattoo ink.

The cosmetic applications could also include hair care type applications. In another particular example, the dispenser of the present invention can be used in a hair dye kit. Certain hair dye kits come in multiple components that are separately stored wherein the dispenser embodiment disclosed herein having a dividing wall that cooperates to define separate chambers can be utilized. Thus, the dispenser of the present invention can be used in a two-part hair care product such as a hair dye kit. A first flowable substance of the hair dye kit can be carried in the first chamber, and a second flowable substance of the hair dye kit can be carried in the second chamber. The membrane is ruptured wherein the two flowable substances can be mixed together to form a mixture or solution. The mixture or solution can then be dispensed from the dispenser onto the hair of a user. The dispenser can also dispense a flowable material or mixture in other hair care products, such as hair bleaches, hair streaking agent, hair highlighter, shampoos, other hair colorants, conditioners, hair gels, mousse, hair removers, or eyebrow dye.

In another example, the dispenser of the present invention can be used in crafting applications or stationary products. The dispenser can also dispense a large variety of stationery or craft products, such as magic markers, glitter gels, glitter markers, glitter glues, gel markers, craft clues, fabric dyes, fabric paints, permanent markers, dry erase markers, dry eraser cleaner, glue sticks, rubber cement, typographic correction fluids, ink dispensers and refills, paint pens, counterfeit bill detection pen, envelope squeeze moisturizers, adhesive label removers, highlighters, and ink jet printer refills.

In another example, the dispenser of the present invention can also dispense a flowable material or mixture that is an electronics-related product. For example, the electronics product could be a cleaning compound, a telephone receiver sanitizer, cell phone cleaner or protectants, a keyboard cleaner, a cassette recorder cleaner, audio/video disc cleaner, a mouse cleaner, or a liquid electrical tape.

In another example, the dispenser of the present invention can dispense a flowable material or mixture in food product applications. For example, the food product may be food additives, food colorings, coffee flavorings, cooling oils, spices, flavor extracts, food additives, drink additives, confections, cake gel, pastry gel, frostings, sprinkles, breath drops, condiments, sauces, liquors, alcohol mixes, energy drinks, or herbal teas and drinks.

In another example, the dispenser of the present invention can be used in home repair product and home improvement applications. The dispenser can also dispense a flowable material that is a home repair product, such as a caulking compounds or materials, a scratch touch up kit, a stain remover, a furniture repair product, a wood glue, a patch lock, screw anchor, wood tone putty or porcelain touch-up. The dispenser could also dispense a plumbing flux applicator, rust remover and tree wound treatment. In certain home repair or home improvement applications, the dispenser can be used in paint applications. The dispenser can dispense a variety of paint products such as general paints including interior/exterior paints, novelty paints, paint additives, wood stain samples, varnishes, stains, lacquers, caulk, paint mask fluid or paint remover.

In another example, the dispenser of the present invention can be used in household related products. For example, the dispenser could be used for cleaning agents, pest control products, a fish tank sealant or a fish tank treatment, a leak sealant, a nut/bolt locker, screw tightener/gap filler, a super glue remover or goo-b-gone. The dispenser could also be used for a colorant dispenser, or disinfectants, a plant food, fertilizers, bug repellants or a cat litter deodorant. The dispenser could also dispense toilet dyes and treatments, eyeglass cleaners, shoe polishes, clothing stain removers, carpet cleaners and spot removers, multi-purpose oils, and ultrasonic cleaner concentrate. The household product could include a variety of pet-related products including but not limited to an animal medicine dispenser, pet medications, animal measured food dispenser, pet shampoos or odor eliminator liquids. A large variety of pest control products can be dispensed by the dispenser, including insect attractants, pesticides, pet insect repellants, pest sterilizers, insect repellants, lady bug attractant and fly trap attractant. The household product could also include various types of polishes, reagents, indicators and other products.

In another example, the dispenser of the present invention can be used in lubricant applications. The dispenser can dispense a large variety of lubricants including industrial lubricants, oils, greases, graphite lubricants or a dielectric grease.

The dispenser of the present invention can also be used in other medical applications including medical related products, medicinal products and medicaments. Additional medical related product applications can include skin adhesive kits to be used in place of traditional stitching products. As discussed, the dispenser could also be used with topical antiseptics, antimicrobials and surgical scrub products. In addition, the dispenser 10 can dispense a large variety of medicinal products, such as blister medicines, cold sore treatments, insect sting and bite relief products, skin cleaning compounds, skin sealing solutions, skin rash lotions, nasal sanitizers, nasal medications, tissue markers, topical antimicrobials, topical demulcent, treatments for acne such as acne medications, umbilical area antiseptics, cough medicines, waterless hand sanitizers, toothache remedies, cold medicines, sublingual dosages or wart treatments. For example, the dispenser could contain a medicinal product containing hydrogen-peroxide used for dermatological conditions such as warts, seborrheic keratosis or similar skin conditions. The dispenser could also be used to dispense compositions for treating various other skin conditions. The dispenser could also be used in conjunction with a medical device product. Other medical related applications could include various types of dental related products including different types of compounds and treatments applied to a patients' teeth. The dispenser could also be used in veterinary related products.

In another example, the dispenser of the present invention can be used in novelty products. For example, the dispenser can contain materials in a glow-stick device. In such instance, the dispenser is a container that may contain multiple components separately stored until activation to create a glowing state in response to mixture of the components. Furthermore, the dispenser can dispense a flowable material or mixture that is a chemiluminescent light, a Christmas tree scent, a glitter gel, and a face paint. Other types of novelty paints could also be used with the dispenser.

In another example, the dispenser of the present invention can be used in sports products. The dispenser can dispense a variety of sports products including sports eye black, football hand glue, and baseball glove conditioner and pine tar. The dispenser can also dispense wildlife lures. The dispenser can be used in various camping related applications including portable lighting fuels for camp lights or other devices and tent repair kits. The dispenser can also be used in bingo or other game markers.

In another example, the dispenser of the present invention can be used in test kit applications. The dispenser can dispense a flowable material or mixture that is a test kit, such as a lead test kit, a drug kit, a radon test kit, a narcotic test kit, a swimming pool test kit (e.g., chlorine, pH, alkalinity etc.), a home water quality tester, a soil test kit, a gas leak detection fluid, a pregnancy tester, or a respirator test kit. The dispenser can also dispense a flowable material or mixture that as part of a medical device test kit, such as a culture media, a drug monitoring system, a microbiological reagent, a *streptococcus* test kit, or a residual disinfectant tester. The dispenser may also be used in diagnostic testing kits, explosive testing kits or other test kits. The dispenser can be used in breathalyzer tests, culture media samples and drug test kits.

In another example, the dispenser of the present invention can be used in personal care products or wellness-related products. The dispenser can also dispense a flowable material or mixture that is a personal care product, such as shaving cream or gel, aftershave lotion, skin conditioner, skin cream, skin moisturizer, petroleum jelly, insect repellant, personal lubricant, ear drops, eye drops, nose drops, corn medications, nail fungal medication, aging liquids, acne cream, contact lens cleaner, denture repair kit, finger nail repair kit, liquid soaps, sun screen, lip balm, tanning cream, self-tanning solutions, eye wash solution finger nail repair kits. The dispenser can also be used with aroma therapy products and homeopathic preparations. The dispenser can also dispense various vitamins, minerals, supplements and pet vitamins.

The dispenser can also dispense a flowable material or mixture in a variety of other miscellaneous applications. Such miscellaneous applications may include, but not be limited to use in connection with a suction device for culture sampling, taking various liquid samples or taking various swabbing samples. The dispenser could also be used for float and sinker devices, dye markers, microbiological reagents, and also for manufacturing parts assembly liquids and irrigation solutions. The dispenser may also be used as a chalk dispenser such as in construction applications.

Thus, the dispenser can be used in many different applications including mechanical, chemical, electrical or biomedical uses. The dispenser can dispense any variety of flowable materials including liquids and powders, and further including a liquid and a powder, two or more powders, or two or more liquids. The dispenser may be used as part of 2-part system (mix before use) including a liquid with a powder, a liquid with a liquid, a powder with a powder, or sealed inside another tube or product container or partially sealed, connected or attached to another container. The dispenser may also be used as part of a plunger dispensing system.

While the invention has been described in its preferred embodiments, it is to be understood that the words which have been used are words of description rather than limitation and that changes may be made within the purview of the appended claims without departing from the true scope and spirit of the invention in its broader aspects.

What is claimed is:

1. A dispenser comprising:
    a first plastic ampoule assembly comprising:
    a container having a first chamber and a second chamber, the first chamber containing a first flowable material, the first chamber having a closed end, the second chamber defining an open end;
    a membrane disposed within the container separating the first chamber and the second chamber, the membrane having a thickness and a weld seam, the weld seam having a thickness less than the thickness of the membrane;
    an applicator positioned in the open end;
    a second plastic ampoule assembly comprising:
    a container having a first chamber and a second chamber, the first chamber containing a second flowable material, the first chamber having a closed end, the second chamber defining an open end;
    a membrane disposed within the container separating the first chamber and the second chamber, the membrane having a thickness and a weld seam, the weld seam having a thickness less than the thickness of the membrane;
    an applicator positioned in the open end;
    wherein the closed end of the first chamber of the first plastic ampoule is connected to the closed end of the first chamber of the second plastic ampoule and defining a connection area.

2. The dispenser of claim 1 wherein the first plastic ampoule assembly and the second plastic ampoule assembly extend away from each other linearly along a longitudinal axis.

3. The dispenser of claim 1 wherein the closed end of the first chamber of the first plastic ampoule has a generally first circular configuration and the closed end of the first chamber of the second plastic ampoule has a generally second circular configuration, wherein the first circular configuration is dimensioned to coincide with a dimension of the second circular configuration.

4. The dispenser of claim 1 wherein the connection between the first plastic ampoule and the second plastic ampoule is an adhesive connection.

5. The dispenser of claim 1 wherein the connection between the first plastic ampoule and the second plastic ampoule is a spin-welded connection.

6. The dispenser of claim 1 further comprising an actuator assembly comprising:
    a base member mounted on the first plastic ampoule and the second plastic ampoule at the connection area;
    an actuator arm having a first arm implement and a central hub, the central hub connected to the base member, the first arm implement having a first intermediate segment having a curvilinear configuration extending away from the base member, the first arm implement having a first depending protrusion at a first distal end, wherein the actuator arm has a second arm implement, the central hub positioned between the first arm implement and the second arm implement, the second arm implement having a second intermediate segment having a curvilinear configuration extending away from the base member generally opposite the first arm implement, the second arm implement having a second depending protrusion at a second distal end, wherein in a first neutral position, the first depending protrusion is positioned proximate the membrane of the first plastic ampoule and in a second neutral position, the second depending protrusion is positioned proximate the membrane of the second plastic ampoule, wherein the first arm implement is pivotable about the base from the first neutral position to a first actuating position that engages and deflects the container of the first plastic ampoule inwardly to fracture the membrane of the first plastic ampoule wherein the flowable material is dispensed from the first plastic ampoule, wherein the second arm implement is pivotable about the base from the second neutral position to a second actuating position that engages and deflects the container of the second plastic ampoule inwardly to fracture the membrane of the second plastic ampoule wherein the second flowable material is dispensed from the second plastic ampoule.

7. The dispenser of claim 6 wherein a proximal end of the first arm implement is connected to the central hub, wherein a first hinge is defined proximate the proximal end of the first arm implement and the central hub, the first hinge defining a cut-out portion that extends into the first arm implement, wherein the first arm implement is pivotable about the first hinge.

8. The dispenser of claim 7 wherein a proximal end of the second arm implement is connected to the central hub, wherein a second hinge is defined proximate the proximal end of the second arm implement and the central hub, the second hinge defining a cut-out portion that extends into the second arm implement, wherein the second arm implement is pivotable about the second hinge.

9. A dispenser and actuator assembly comprising:
a glass ampoule assembly comprising:
a first crushable glass ampoule containing a first flowable material;
a second crushable glass ampoule containing a second flowable material;
a resilient plastic outer container, the outer container having a first open end and a second open end, the outer container receiving the first glass ampoule and the second glass ampoule;
a first applicator positioned in the first open end;
a second applicator positioned in the second open end;
an actuator assembly comprising:
a base member having an annular ring, the annular ring receiving the outer container and mounted on the outer container;
an actuator arm having a first arm implement and a central hub, the central hub connected to the base member, the first arm implement having a first intermediate segment having a curvilinear configuration extending away from the base member, the first arm implement having a first depending protrusion at a first distal end, the first depending protrusion positioned proximate the first glass ampoule, wherein the actuator arm has a second arm implement, the central hub positioned between the first arm implement and the second arm implement, the second arm implement having a second intermediate segment having a curvilinear configuration extending away from the base member generally opposite the first arm implement, the second arm implement having a second depending protrusion at a second distal end, the second depending protrusion positioned proximate the second glass ampoule,
wherein the first arm implement is pivotable with respect to the base member from a first neutral position to a first actuating position to engage and deflect the outer container inwardly to crush the first glass ampoule wherein the first flowable material is released from the first glass ampoule and into the first applicator to be dispensed, wherein the second arm implement is pivotable with respect to the base member from a second neutral position to a second actuating position to engage and deflect the outer container inwardly to crush the second glass ampoule wherein the second flowable material is released from the second glass ampoule and into the second applicator to be dispensed.

10. The dispenser and actuator assembly of claim 9 wherein the outer container has a dividing wall defining a first chamber having the first open end and defining a second chamber having the second open end, the first glass ampoule positioned in the first chamber and the second glass ampoule positioned in the second chamber.

11. The dispenser and actuator assembly of claim 9 wherein the actuator assembly is slidably moveable along the outer container.

12. The dispenser and actuator assembly of claim 9 wherein a proximal end of the first arm implement is connected to the central hub, wherein a first hinge is defined proximate the proximal end of the first arm implement and the central hub, the first hinge defining a cut-out portion that extends into the first arm implement, the first arm implement being pivotable about the first hinge.

13. The dispenser and actuator assembly of claim 12 wherein a proximal end of the second arm implement is connected to the central hub, wherein a second hinge is defined proximate the proximal end of the second arm implement and the central hub, the second hinge defining a cut-out portion that extends into the second arm implement, the second arm implement being pivotable about the second hinge.

14. The dispenser and actuator assembly of claim 13 further comprising a second actuator arm having a first arm implement and a second central hub, the second central hub connected to the base member generally opposite to the central hub, the first arm implement of the second actuator arm having a first intermediate segment having a curvilinear configuration extending away from the base member, the first arm implement of the second actuator arm having a first depending protrusion at a first distal end, wherein the first arm implement of the second actuator arm is pivotable with respect to the base member from a first neutral position to a first actuating position to engage and deflect the outer container inwardly to crush the first glass ampoule wherein the first flowable material is released from the first glass ampoule and into the first applicator to be dispensed.

15. The dispenser actuator assembly of claim 14 wherein the second actuator arm has a second arm implement, the second central hub positioned between the first arm implement and the second arm implement of the second actuator arm, the second arm implement of the second actuator arm having a second intermediate segment having a curvilinear configuration extending away from the base member generally opposite the first arm implement, the second arm implement of the second actuator arm having a second depending protrusion at a second distal end, wherein the second arm implement of the second actuator arm is pivotable with respect to the base member from a second neutral position to a second actuating position to engage and deflect the outer container inwardly to crush the second glass ampoule wherein the second flowable material is released from the second glass ampoule and into the second applicator to be dispensed.

16. The dispenser and actuator assembly of claim 15 wherein the first arm implement of the first actuator arm is positioned generally opposite to the first arm implement of the second actuator arm.

17. The dispenser and actuator assembly of claim 16 wherein the second arm implement of the first actuator arm is positioned generally opposite to the second arm implement of the second actuator arm.

18. The dispenser and actuator assembly of claim 17 wherein the first glass ampoule has a first dome-shaped end and an intermediate section wherein an interface area is defined proximate a juncture between the first dome-shaped end and an end of the intermediate section wherein the first depending protrusion of the first arm implement of the first actuator arm and the first depending protrusion of the first arm implement of the second actuator arm are configured to engage and deflect the outer container inwardly to crush the glass ampoule at the interface area.

19. The dispenser and actuator assembly of claim 18 wherein the second depending protrusion of the second arm implement of the first actuator arm and the second depending protrusion of the second arm implement of the second actuator arm are configured to engage and deflect the outer container inwardly to assist in manipulating the flowable material into the applicator to be dispensed from the glass ampoule assembly.

20. The dispenser and actuator assembly of claim 19 wherein the first applicator has a first applicator structure, and the second applicator has a second applicator structure, the second applicator structure being different from the first applicator structure.

21. A glass ampoule assembly comprising:
a single crushable glass ampoule containing a flowable material;
a resilient plastic outer container, the outer container having a first open end and a second open end, the outer container receiving the glass ampoule through one of the first open end and the second open end;
a first applicator positioned in the first open end, the first applicator having a first applicator structure; and
a second applicator positioned in the second open end, the second applicator having a second applicator structure, the second applicator structure being different from the first applicator structure, wherein the first applicator is a swab assembly and the second applicator is a dropper assembly.

22. A dispenser comprising:
an outer container having a dividing wall defining a first chamber having a first open end and defining a second chamber having a second open end;
a first rupturable ampoule containing a first flowable material, the first rupturable ampoule positioned in the first chamber;
a second rupturable ampoule containing a second flowable material, the second rupturable ampoule positioned in the second chamber;
a first applicator positioned in the first open end; and
a second applicator positioned in the second open end,
wherein the outer container is deflectable inwardly to rupture the first rupturable ampoule wherein the first flowable material is released from the first ampoule and into the first applicator to be dispensed, and wherein the outer container is deflectable inwardly to rupture the second rupturable ampoule wherein the second flowable material is released from the second ampoule and into the second applicator to be dispensed, and further comprising an actuator assembly comprising:

a base member mounted on the outer container;

an actuator arm having a first arm implement and a central hub, the central hub connected to the base member, the first arm implement having a first intermediate segment having a curvilinear configuration extending away from the base member, the first arm implement having a first depending protrusion at a first distal end, wherein the actuator arm has a second arm implement, the central hub positioned between the first arm implement and the second arm implement, the second arm implement having a second intermediate segment having a curvilinear configuration extending away from the base member generally opposite the first arm implement, the second arm implement having a second depending protrusion at a second distal end, wherein in a first neutral position, the first depending protrusion is positioned proximate the first ampoule and in a second neutral position, the second depending protrusion is positioned proximate the second ampoule, wherein the first arm implement is pivotable about the base from the first neutral position to a first actuating position that engages and deflects the container inwardly to rupture the first ampoule wherein the flowable material is released from the first ampoule and into the first applicator to be dispensed, wherein the second arm implement is pivotable about the base from the second neutral position to a second actuating position that engages and deflects the container inwardly to rupture the second ampoule wherein the second flowable material is released from the second ampoule and into the second applicator to be dispensed.

23. The dispenser of claim 22 wherein the first rupturable ampoule is a first glass ampoule.

24. The dispenser of claim 22 wherein the second rupturable ampoule is a second glass ampoule.

25. The dispenser of claim 22 wherein the first applicator is a first swab.

26. The dispenser of claim 22 wherein the second applicator is a second swab.

27. The dispenser of claim 22 wherein the first applicator and the second applicator are positioned on the outer container at opposed distal ends of the outer container.

* * * * *